(12) United States Patent
Smith-Swintosky et al.

(10) Patent No.: US 8,497,298 B2
(45) Date of Patent: Jul. 30, 2013

(54) USE OF BENZO-FUSED HETEROCYCLE SULFAMIDE DERIVATIVES FOR LOWERING LIPIDS AND LOWERING BLOOD GLUCOSE LEVELS

(75) Inventors: Virginia L. Smith-Swintosky, Hatfield, PA (US); Allen B. Reitz, Lansdale, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 11/611,961

(22) Filed: Dec. 18, 2006

(65) Prior Publication Data

US 2007/0155821 A1   Jul. 5, 2007

Related U.S. Application Data

(60) Provisional application No. 60/751,677, filed on Dec. 19, 2005.

(51) Int. Cl.
*A61K 31/335* (2006.01)
*A61K 31/16* (2006.01)

(52) U.S. Cl.
USPC ........... 514/450; 514/452; 514/463; 514/600; 514/866

(58) Field of Classification Search
USPC .................. 514/450, 452, 463, 600, 866
See application file for complete search history.

(56) References Cited

U.S. PATENT DOCUMENTS

| | | | |
|---|---|---|---|
| 2,527,861 A | 10/1950 | Walter | |
| 3,143,549 A | 8/1964 | Lafferty et al. | |
| 3,318,952 A | 5/1967 | Houlihan | |
| 3,383,414 A | 5/1968 | Houlihan | |
| 3,539,573 A | 11/1970 | Schmutz | |
| 3,621,096 A | 11/1971 | Prange et al. | |
| 4,513,006 A | 4/1985 | Maryanoff et al. | |
| 4,539,413 A | 9/1985 | Mouzin et al. | |
| 4,710,500 A | 12/1987 | Perregaard | |
| 4,804,663 A | 2/1989 | Kennis et al. | |
| 4,831,031 A | 5/1989 | Lowe, III et al. | |
| 4,879,288 A | 11/1989 | Warawa et al. | |
| 5,112,838 A | 5/1992 | Perregaard et al. | |
| 5,158,952 A | 10/1992 | Janssen et al. | |
| 5,192,785 A | 3/1993 | Lo et al. | |
| 5,194,446 A | 3/1993 | Lo et al. | |
| 5,212,326 A | 5/1993 | Meade | |
| 5,229,382 A | 7/1993 | Chakrabarti et al. | |
| 5,238,945 A | 8/1993 | Perregaard et al. | |
| 5,242,942 A | 9/1993 | Costanzo et al. | |
| 5,258,402 A | 11/1993 | Maryanoff | |
| 5,273,993 A | 12/1993 | Lo et al. | |
| 5,312,925 A | 5/1994 | Allen et al. | |
| 5,384,327 A | 1/1995 | Costanzo et al. | |
| 5,387,700 A | 2/1995 | Maryanoff et al. | |
| 5,731,348 A | 3/1998 | Gu et al. | |
| 5,753,693 A | 5/1998 | Shank | |
| 5,753,694 A | 5/1998 | Shank | |
| 5,760,007 A | 6/1998 | Shank et al. | |
| 5,780,650 A | 7/1998 | Furukawa et al. | |
| 5,935,933 A | 8/1999 | Shank et al. | |
| 5,998,380 A | 12/1999 | Ehrenberg et al. | |
| 6,071,537 A | 6/2000 | Shank | |
| 6,150,419 A | 11/2000 | Fairbanks et al. | |
| 6,187,338 B1 | 2/2001 | Caruso et al. | |
| 6,191,163 B1 | 2/2001 | Coltrell | |
| 6,211,241 B1 | 4/2001 | Islam et al. | |
| 6,319,903 B1 | 11/2001 | Carrazana et al. | |
| 6,322,503 B1 | 11/2001 | Sparhawk, Jr. | |
| 6,323,236 B2 | 11/2001 | McElroy | |
| 6,391,877 B1 | 5/2002 | Islam et al. | |
| 6,503,884 B1 | 1/2003 | Ehrenberg et al. | |
| 6,559,293 B1 | 5/2003 | Almarsson et al. | |
| 6,562,865 B1 | 5/2003 | Codd et al. | |
| 6,583,172 B1 | 6/2003 | Shank | |
| 6,627,653 B2 | 9/2003 | Plata-Salaman et al. | |
| 6,852,701 B2 | 2/2005 | Plata-Salaman et al. | |
| 6,852,738 B2 | 2/2005 | Jones et al. | |
| 6,949,518 B1 | 9/2005 | Chu | |
| 2001/0008889 A1 | 7/2001 | Caruso et al. | |
| 2002/0015713 A1 | 2/2002 | Murdock et al. | |
| 2004/0073037 A1 | 4/2004 | Jones et al. | |
| 2004/0192690 A1 | 9/2004 | Buxton et al. | |
| 2004/0253223 A1 | 12/2004 | Rodriguez | |
| 2005/0148603 A1 | 7/2005 | Jimenez et al. | |
| 2005/0282887 A1 | 12/2005 | McComsey et al. | |
| 2006/0047001 A1 | 3/2006 | Parker et al. | |
| 2006/0241172 A1 | 10/2006 | Zhou et al. | |
| 2006/0270856 A1 | 11/2006 | Abdel-Magid | |
| 2006/0276528 A1 | 12/2006 | Abdel-Magid et al. | |
| 2007/0293440 A1 | 12/2007 | Smith-Swintosky et al. | |
| 2007/0293476 A1 | 12/2007 | Smith-Swintosky et al. | |
| 2009/0182141 A1 | 7/2009 | Abdel-Magid et al. | |
| 2009/0209634 A1 | 8/2009 | Smith-Swintosky | |
| 2009/0247617 A1 | 10/2009 | Abdel-Magid et al. | |
| 2009/0247618 A1 | 10/2009 | Ballentine et al. | |

(Continued)

FOREIGN PATENT DOCUMENTS

| | | |
|---|---|---|
| CA | 2416647 A | 1/2003 |
| DE | 1211166 | 2/1966 |

(Continued)

OTHER PUBLICATIONS

Maryanoff et al.: Anticonvulsant O-Alkyl Sulfamates 2,3:4,5-Bis-O-(1-methylethylidene)-betas-D-fructopyranose Sulfamate and Related Compounds, J.Med. Chem., vol. 30, No. 5, 1987, pp. 880-887.

(Continued)

*Primary Examiner* — Kevin Weddington
(74) *Attorney, Agent, or Firm* — Hal B. Woodrow

(57) ABSTRACT

The present invention is a method for the glucose related disorders and lipid related disorders comprising administering to a subject in need thereof a therapeutically effective amount of one or more novel benzo-fused heterocycle sulfamide derivatives of formula (I) or formula (II) as herein defined. The present invention is further directed to methods of treatment comprising co-therapy with an anti-diabetic agent, and anti-lipid agent and/or an anti-obesity agent.

10 Claims, No Drawings

U.S. PATENT DOCUMENTS

| | | | |
|---|---|---|---|
| 2009/0318544 A1 | 12/2009 | Mehrman et al. | |
| 2010/0063138 A1 | 3/2010 | McComsey et al. | |

FOREIGN PATENT DOCUMENTS

| | | | |
|---|---|---|---|
| DE | 2022370 | | 12/1971 |
| DK | 9800727 | A | 5/1998 |
| EP | 0138441 | B1 | 4/1985 |
| EP | 0483881 | B1 | 5/1992 |
| EP | 490689 | | 6/1992 |
| EP | 498770 | | 8/1992 |
| EP | 503440 | A1 | 9/1992 |
| EP | 0478954 | | 10/2000 |
| EP | 1056733 | | 12/2000 |
| EP | 1118610 | | 7/2001 |
| GB | 1087602 | | 10/1967 |
| GB | 1111706 | | 5/1968 |
| RU | 2226357 | | 4/2004 |
| RU | 2246727 | | 8/2004 |
| WO | 94/14827 | A1 | 7/1994 |
| WO | 95/17406 | A1 | 6/1995 |
| WO | 96/06822 | A1 | 3/1996 |
| WO | 97/13510 | A1 | 4/1997 |
| WO | 97/19919 | | 6/1997 |
| WO | WO 97/19682 | A1 | 6/1997 |
| WO | 97/35584 | A1 | 10/1997 |
| WO | 98/00123 | | 1/1998 |
| WO | 98/00124 | A1 | 1/1998 |
| WO | 98/00131 | A1 | 1/1998 |
| WO | WO 98/00130 | A2 | 1/1998 |
| WO | 98/06708 | A1 | 2/1998 |
| WO | 98/07447 | A1 | 2/1998 |
| WO | WO 98/15270 | | 4/1998 |
| WO | WO 99/44581 | A2 | 9/1999 |
| WO | 99/62522 | | 12/1999 |
| WO | 00/01376 | A2 | 1/2000 |
| WO | 00/07583 | A2 | 2/2000 |
| WO | 00/42995 | A2 | 7/2000 |
| WO | 00/42996 | A2 | 7/2000 |
| WO | 00/49017 | | 8/2000 |
| WO | WO 00/50020 | A2 | 8/2000 |
| WO | 00/54588 | A1 | 9/2000 |
| WO | 00/61137 | | 10/2000 |
| WO | WO 00/61139 | A1 | 10/2000 |
| WO | WO 00/61140 | A1 | 10/2000 |
| WO | 00/66109 | A2 | 11/2000 |
| WO | WO 00/76493 | A1 | 12/2000 |
| WO | 01/13904 | A2 | 3/2001 |
| WO | 01/76576 | A2 | 10/2001 |
| WO | 02/03984 | | 1/2002 |
| WO | WO 02/07821 | A | 1/2002 |
| WO | 02/09694 | | 2/2002 |
| WO | 02/30881 | | 4/2002 |
| WO | 02/089785 | | 11/2002 |
| WO | WO 02/096424 | A1 | 12/2002 |
| WO | 2004/014352 | | 2/2004 |
| WO | WO 2004/093912 | A1 | 4/2004 |
| WO | WO 2004/092116 | A1 | 10/2004 |
| WO | WO 2004/096771 | A1 | 11/2004 |
| WO | WO 2004/098584 | A1 | 11/2004 |
| WO | WO 2005/020917 | A2 | 3/2005 |
| WO | 2006/007436 | | 1/2006 |
| WO | WO 2006/007435 | | 1/2006 |
| WO | WO 2006/010008 | A1 | 1/2006 |
| WO | WO 2006/010750 | A1 | 2/2006 |
| WO | WO 2006/023861 | A1 | 3/2006 |
| WO | 2006/127184 | | 11/2006 |
| WO | 2007/075695 | | 7/2007 |
| WO | 2007/075698 | | 7/2007 |
| WO | 2007/075717 | | 7/2007 |
| WO | 2007/075751 | | 7/2007 |
| WO | 2007/075752 | | 7/2007 |
| WO | 2007/075833 | | 7/2007 |
| WO | 2007/075834 | | 7/2007 |
| WO | 2007/092086 | | 8/2007 |
| WO | 2007/095615 | | 8/2007 |
| WO | 2007/095618 | | 8/2007 |
| WO | 2007/098486 | | 8/2007 |
| WO | 2007/137167 | | 11/2007 |
| WO | 2009/089210 | | 7/2009 |
| WO | 2009/120191 | | 10/2009 |
| WO | 2009/120192 | | 10/2009 |

OTHER PUBLICATIONS

Maryanoff et al.: "Comparison of Sulfamates and Sulfamide Groups for the Inhibition of Carbonci Anhydrase-II by Using Topiratmate as a Structural Platform", J. Med. Chem, vol. 48, No. 6, 2004, pp. 1941-1947.

Levy RH et al., eds. Antiepileptic Drugs. 3$^{rd}$ ed. New York: Raven Press, 1989:85-102.

Scozzafava A et al, "Modulaton of Carbonic Anhydrase Activity and Its Applications in Therapy", Expert Opinion on Therapeutic Patents 2003 United Kingdom, vol. 14, No. 5 (2004) pp. 667-702, XP002331413, ISSN:1354-3776.

Edwards, KR; Glantz, MJ; Button, J et al, Evaluation of Topiramate in The Management of Painful Diabetic Neuropathy. Presented at: 18$^{th}$ Annual Meeting of the American Pain Society; Oct. 1999, Fort Lauderdale, FL.

York, DA et al, "Effects of Topirament on High Fat Diet-Induced Obesity", FASEB journal, Fed. Of America Soc. For Experimental Biology, Bethesda, MD, US., vol. 14, No. 4, Apr. 2000. p. A431, XP000915192.

The Merck Manual, 1999, Merck Research, Whitehouse Station, NJ XP002224345, Diabetes Mellitus, pp. 165-177.

Edwards, K.R. et al, Efficacy and safety of topiramate in the treatment of painful diabetic neuropathy: a double-blind placebo-controlled study ADIS Title: Topiramate: therapeutic use: Neurogenic pain; In patients with diabetic neuropathy: Neurology 54 (Suppl. 3): 81 Apr. 11, 2001.

Crooke et al, Abstract, Topiramate Improves Glycemic Control Independent of Weight Loss in ob/ob Mice.diabetes. A Journal of the American Diabetes Association, Abstract Book 61$^{st}$ Scientific Sessions Friday, Jun. 22-Tuesday Jun. 26, 2001, 2158-PO, A513.

Demarest et al, Abstract, Topiramate Improves Glucose Tolerance and May Improve Insulin Sensitivity in Animal Models of Type 2 Diabetes Mellitus, diabetes, A Journal of the American Diabetes Association, Abstract Book 61$^{st}$ Scientific Sessions Friday, Jun. 22-Tuesday Jun. 26, 2001, 1254-P, A302.

Osborne et al, Abstract, Topiramate Improves Glycemic Control and Triglycerides in Animal Models 1 page The Posters were presented at the American Diabetes Association Conference held Jun. 22-26 in Philadelphia, diabetes, A Journal of the American Diabetes Association, Abstract Book 61$^{st}$ Scientific Sessions Friday, Jun. 22-Tuesday Jun. 26, 2001, 1255-P, A302.

Emancipator K., "Laboratory Diagnosis and Monitoring of Diabetes Mellitus", Am J Clin Pathol, 112(5):665-74 1999.

Caumo A., "Insulin Sensitivity from Meal Tolerance Tests In Normal Subjects: A Minimal Model Index", J Clin Endocrinol Metab, 85(11):4396-402 2000.

Haffner S.M., "Impaired Glucose Tolerance, Insulin Resistance and Cardiovascular Disease", Diabetic Medicine, Aug. 1977;14 Suppl 3:S12-8.

Goldberg R.G., "Prevention of Type 2 Diabetes", Med Clin North Am, Jul. 1998;82(4):805-21.

Groop L., "Characterization of the Prediabetic State", Am J Hypertension; Sep. 1997;10(9 Pt 2):172S-180S.

Haffner S.M., "The Prediabetic Problem: Development of Non-Insulin-Dependent Diabetes Mellitus and Related Abonormalities", J Diabetes Complications, Mar.-Apr. 1997;11(2):69-76.

Beck-Nielsen H., "In Vivo Glucose Metabolism, Insulin Secretion and, Insulin Action in Europids with Non-insulin-dependent Diabetes Mellitus (NIDDM) and Their First-degree Relatives", Diabet Med Sep. 1996;13(9 Suppl 6):S78-84.

Dinneen S.F., "The Postprandial State: Mechanism of Glucose Intolerance", Diabet Med Aug. 1997;14 Suppl 3:S19-24.

Ramlo-Halsted BA, "The Natural History of Type 2 Diabetes", Primary Care Dec. 1999;26(4):771-89.

Kawasaki, "Structural and functional analysis of pancreatic islets preserved by pioglitazone in db/db mice", Am J Physiol Endocrinol Metab; 2004, p. E510-E518, doi 10.1152/ajpendo.00128.2004.

American Diabetes Association, "Definition and Description of Diabetes Mellitus", Diabetes Care, Jan. 2006; p. S43-S48, vol. 29 Supplement 1.

BESAG FMC: "Behavioural Effects of the New Anticonvulsants" Drug Safety, Adis Press, Auckland, NZ, vol. 24, No. 7, 2001, pp. 513-536.

Guillaume et al., "Glial contribution to seizure: Carbonic anhydrase activity in epileptic mammalian brain" Epilepsia, 1991, vol. 32, No. 1, 1991, pp. 10-15.

Johnson, B., "Progress in the development of topiramate for treating alcohol dependence: From a hypothesis to a proof-of-concept study" Alcoholism: Clinical and Experimental Research, vol. 28, No. 8, 2004, pp. 1137-1144.

Klinger et al., "Inhibition of carbonic anhydrase-II by sulfamate and sulfamide groups: An investigation involving direct thermodynamic binding measurements" Journal of Medicinal Chemistry, vol. 49, No. 12, Jun. 15, 2006, pp. 3496-3500.

Mula et al., "The role of anticonvulsant drugs in anxiety disorders: a critical review of the eVidence" Journal of Clinical Psychopharmacology, Williams and Wilkins, vo 1. 27, No. 3, 2007, pp. 263-272.

Nies et al., Goodman & Gilman's The Pharmacological Basis of Therapeutics, 9th Edition, pp. 43-62, 1996.

Raguraman, et al., "Effects of topiramate in alcohol dependence [2]" Australian and New Zealand Journal of Psychiatry, vol. 39, No. 8, 2005, pp. 736-737.

Shank et al., "Examination of two independent kinetic assays for determining the inhibition of carbonic anhydrases I and II: Structure-activity comparison of sulfamates and sulfamides" Chemical Biology and Drug Design, vol. 68, No. 2, 2006, pp. 113-119.

Tenovuo, O., "Central acetylcholinesterase inhibitors in the treatment of chronic traumatic brain injury—Clinical experience in 111 patients" Progress in Neuro-Psychopharmacology and Biological Psychiatry, 2005, vol. 29, No. 1, Jan. 2005, pp. 61-67.

Waugh et al., "Topiramate: As Monotherapy in Newly Diagnosed Epilepsy" CNS Drugs, vol. 17, No. 13, 2003, pp. 985-992.

Sharma K, McCue P, Dunn SR. Am J Physiol Renal Physiol. Jun. 2003;284(6):F1138-44.

Aeberli, P. et al. "Neuropharmacological Investigation of N-Benzylsulfamides", Journal of Medicinal Chemistry, Jul. 1967, vol. 10, No. 4, pp. 636-642.

Garonna, F. et al., "Topiramate in the treatment of overweight/obese binge eaters ADIS Title: Topiramate: therapeutic use; Obseity; In patient with binge eating disorders" International Journal of Neuropsychopharmacology 3(Suppl 1): 299: Jul. 2000 XP001030426 Bassano dG Vicenza Italy.

Penovich et al., "Weight Loss in Patients Receiving Topiramate for Intractable Epilepsy", 1994, Neurology 44 (Suppl. 2) Abstract 309P, 46th Annual Meeting of the American Academy of Neurology, Washington, D.C.

Pini et al., "Anti-Epileptic Drugs in the Preventive Treatment of Migraine Headache: a Brief Review", (J. Headache Pain, 2001, 2:13-19.

Rogaswki et al., Nature Medicine, vol. 10, No. 7, Jul. 2004, pp. 685-692.

Notice of Allowance dated Dec. 31, 2008 in U.S. Appl. No. 11/154,443.

Office Action mailed Aug. 5, 2008 in U.S. Appl. No. 11/612,146.

Ambrosini, P.J., Psychiatr. Serv. 2000, 51, 627-633.

Ananth, J., Psychother. Psychosom. 1998, 67, 61-70.

Angehagen, Mikael et al., "Does topiramate (TPM) have protective effects on astroglia cells and neurons in primary cortical cultures", Epilepsia, (1998) vol. 39, No Suppl 6, pp. 44, XP000923162 abstract 2.050.

Ayata et al., "Suppression of cortical Spreading Depression in Migraine Prophylaxis", Ann Neurol 2006; 59:652-661.

Barry et al. Current status of the utilization of antiepileptic treatmetns in mood, anxiety and aggression: drugs and devices, Jan. 2004, 35, 1.

Berman, R.M. et al., Depress. Anxiety 1997, 5, 154-164.

Breslau et al., "The impact of migraine. Epidemiology, risk factors, and co-morbidities" Neurology, 2001;56:S4-S12 (Abstract only).

Burton et al. Anti-epileptic drugs for pain management. Pain, Symptom, Control and Palliative Care, 2001, vol. 1, No. 2.

Cadieux, R.J., Am. Fam. Physician 1998, 58, 2059-2062.

Calabrese, J.R. et al., Eur. Neuropsychopharmacol. 1999, 9, S109-S112.

Calabresi et al., "Antiepileptic drugs in migraine: from clinical aspects to cellular mechanisms", Trends in Pharmacological Sciences, vol. 28, No. 4, 188-195 (2007).

Cavaletti G et al: "Experimental peripheral neuropathy induced in adult rats by repeated intraperitoneal administration of Taxal", Exper Neurol 133:64-72, 1995.

Chaplan SR et al: "Quantitative assessment of tactile allodynia in the rat paw". J Neurosci Meth, 53:55-63, 1994.

Diamond et al, "Practical Approaches to Migraine Management", 2002, CNS Drugs, 16(6), pp. 385-403.

Dickenson et al. Neurobiology of neuropathic pain: mode of action of anticonvulsants. European Journal of Pain, 2002, 6 (Suppl. A): 51-60, 2002.

Drach, B.S. et al.: "N-1,2,2,2,-tetra-chloroethyl-N',N'-dimethylsulphamide". Journal of Organic Chemistry of the USSR., vol. 13, No. 7, Jul. 1977, pp. 1289-1294, XP008067470.

Dressler et al., Benzodiazepine in geriatric patients . . . , Abstract, Anaesthesiologie and reanimation, 1996, vol. 21/5, pp. 136-138.

Drug Facts and Comparison (1995 Edition, pp. 1607).

Dursun, S.M. et al., "Accelerated weight loss after treating refractory depression with fluoxetine plus topiramate: possible mechanisms of action?", The Canadian Journal of Psychiatry, vol. 46, No. 3, pp. 287-288, 2001.

Erfurth, Andreas et al., "Bupropion as add-on strategy in difficult-to-treat bipolar depressive patients", Neuropsychobiology, vol. 45, No. Sup 1, pp. 33-36, 2002.

Fakhoury et al., Epilepsy Behay. Aug. 2007, abstract.

Flatters, SJL et al: "Acetyl-L-carnitine prevents and reduces paclitaxel-induced painful peripheralneuropathy", Neurosci Lett 397:219-223, 2006.

Gareri, P. et al, Progress in Neurobiology 61, 2000, 353-396.

Ghaemi et al., Soc. of Bio. Psychiatry, (1999) vol. 45, 137-144.

Gorelick D A, "Pharmacological treatment" Recent Developments in Alcoholism, vol. 11, 1993, p. 413-427, XP00913482 p. 417.

Gorelick et al., Drugs 2004: 64(14), pp. 1547-1573.

Grond et al., "Weak Opioids—an educational substitute for morphine?", Current Opinion in Anaesthesiology, vol. 11, No. 5, 1998, pp. 559-565 XP00982759.

Harrison's Principles of Internal Medicine, Isselbacher et al. eds. McGraw-Hill, Inc., New York, 1994, p. 69.

Harrison'S Principles of Internal Medicine, vol. 2, 23d ed., Ed by Isselbacher, Braunwald, Wilson, Martin, Fauci and Kasper, McGraw-Hill Inc New York City, 1994, p. 2275.

Hatzinger, M. et al., Wien. Med. Wochenschr. 1999, 149, 511-514.

Hauner H, "Managing type 2 diabetes mellitus in patients with obesity," Treatments in Endocrinology, 2004, 3(4), 223-232 (only abstract provided).

Headache Classification Committee of the International Headache Society. Cephalalgia 1988;8 Suppl 7:1-96.

Hering et al., "Sodium valproate in the treatment of cluster headache", Cephalalgia (Sep. 1989) 9(3) pp. 195-198.

Huisman, M. et al.:"Synthesis of N-(diemthylsulphamoyl)aldimines, a new type of aldimine derivative". Synthetic Communications, vol. 27, No. 6, 1997, pp. 945-952.

Jay et al., "Epilepsy, Migraine and EEG Abnormalities in Children: a Review & Hypothesis," Journal of Head and Face Pain, abstract, vol. 22, Issue 3, pp. 110-114, 1982.

Joffe, R.T. et al., Arch. Gen. Psychiatry 1993, 50, 397-393.

Johns Hopkins Clinical Trial of Topiramate for Cocaine Addiction (ClinicalTrials.gov), (2009).

Johnson, SA CNS Drugs, 2005. vol. 19, No. 1 0, pp. 873-896.

Keck, P et al, "Valproate and carbamazepine in the treatment of panic and post traumatic stress disorders, withdrawals states . . . " J Clin Psychopharm, vol. 12, No. 1, p. 36S-41S (2002).

Kent, J.M., Lancet 2000, 355, 911-918.

Ketter, T.A. et al., J. Clin. Psychiatry 1995, 56, 471-475.

Keung W.M. et al, "Daidzin and daidzein suppress free-choice ethanol intake by Syrian golden hamsters" Proc Natl Acad Sci, vol. 90, p. 1008-10012, Nov. 1993.
Kohno, H. et al.: "A Novel Synthesis of Isoquinolines Containing an Electron Withdrawing Substitute". Heterocycles, vol. 51, No. 1, 1999, pp. 103-117, XP008052600.
Kralinsky E.A. Tramal in the treatment of pain in children with malignancies XP002162259 English Abstract & Klinicka Onkologie, vol. 7, No. 6, 1994, pp. 182-185.
Kunkler et al., "Hippocampal Spreading Depression Bilaterally Activates the Caudal Trigeminal Nucleus in Roadent", Hippocampus 13:835-844 (2003).
Kuzniecky et al., "Topiramate increases cerebral GABA in healthy humans", Neurology (Aug. 1998) 51(2) pp. 627-629.
Kyowa Hakko, "Topiramate" Drugs of the Future, ES, Barcelona, vol. 21, No. 4, Jan. 1, 1996; p. 463-465, XP002043895.
Langtry H.D. et al, "Topiramate, A review of its pharmacodynamic and pharmacokinetic properties and clinical efficacy in the management of epilepsy" Drugs, (1997) 54/5 pp. 752-773, XP002179441.
Lydiard, R.B. et al., J. Clin. Psychiatry 1998, 59, Suppl. 18, 10-17.
Malatynska et al., "Dominant-submissive behavior as models of mania and depression", Neuroscience and Biobehavioral Review, 29 (2005) 715-737.
Malatynska et al., "Submissive behavior in mice as a test for antidepressant drug activity", Neuroscience and Biobehavioral Review, 82 (2005) 306-313.
Maryanoff, B.E. et al.: "Structure-Activity Studies on Anticonvulsant Sugar Sulphmates Related to Topiramate. Enhanced Potency with Cyclic Sulphate Derivatives". Journal of Medicinal Chemistry, vol. 41, No. 8, 1998, pp. 1315-1343, XP002149867.
Mathew, Ninan T., MD, et al, "Prophylaxis of Migraine, Transformed Migraine, and Cluster Headache with Topiramate" Headache (2002), (42)796-803.
Mathew, N. T. "Antiepileptic Drugs in Migraine Prevention", 2001, Headache, November/December Suppl 2001, pp. S18-S24.
Mazzotta et al., J Headache Pain, 2004 5:S67-S70.
McElroy, S.L. et al., "A pilot trial of adjunctive topiramate in the treatment of bipolar disorder ADIS Title: Topiramate: therapeutic use; Bipolar disorder: A pilot trial of adjunctive treatment" retrieved from STN Database Accession No. 1998:39968 XP00217779443 Abstract & XXIST CINP Congress (Jul. 12, 1998) pp. 281 (Poster) University of Cincinnati College of Medicine, Cincinnati, OH.
Meldrum B. et al., "Excitatory amino acid neurotoxicity and neurodegenerative disease" TIPS, vol. 11, 1990, pp. 379-387, XP000915223.
Migraine: Treatments and drugs, by Mayo Clinic Staff, http://www.mayoclinic.com/health/migraineheadache/DS00120/DSECTION=treatments-and-drugs, (2010).
Mueller T I, "A double-blind, placebo-controlled pilot study of carbamazepine for the treatment of alcohol dependence", Alcoholism Clin Exp Res, vol. 21, No. 1, 1997, p. 86-92, X00913485.
Moller, H.J. et al., Eur. Arch. Psychiatry Clin. Neurosci. 2000, 250, 57-68.
Moskowitz, M.A., "The Neurobiology of Vascular Head Pain", Annals of Neurology, vol. 16, Issue 2, pp. 157-168, 1984.
Myers, R.D., "New Drugs for the Treatment of Experimental Alcoholism", Alcohol, vol. 11, No. 6, 1994, p. 439-451.
Nemeroff, C.B., Depress. Anxiety 1996-1997, 4, 169-181.
Olesen et al., "Spreading Cerebral Oligemia in Classical- and Normal Cerebral Blood Flow in Common Migraine", Department of Neuromedicine, Rigshospitalet 2100 Copenhagen, Denmark, Jan 28, 1982 (Headache 22:242-248, 1982).
Olson et al [Editors]. Remington's Pharmaceutical Sciences, pp. 420-425, 1980.
Ottman et al., "Comorbidity of migraine and epilepsy", Neurology, 1994;44: 2105 (Abstract only).
Pansare, S.V. et al.: "Intramolecular Imine Cross-Coupling in Dibenzylidine Sulphamides; synthesis of unsymmetrical 1,2-diaryl ethanediamines". Tetrahedron Letters, vol. 37, No. 16, Apr. 15, 1996, pp. 2859-2862, XP004029817.
Pascual D et al: "A cannabinoid agonist, WIN55,212-2, reduces neuropathic nociciption induced by paclitaxel in rats" Pain 118:23-34, 2005.

Perry et al. "Sumatriptan: An Updated Review of its Use in Migraine", 1998, Drugs, vol. 55, No. 6, pp. 889-922.
Polomano et al: "A painful peripheral neuropathy in the rat produced by the chemotherapeutic drug, paclitaxel", Pain, 94:293-304, 2001.
Prado Lima, P.A.S. et al., "Topiramate in treatment-refractory depression" retrieved from STN Database accession No. 1999:61852 XP002179442 Abstract & 11th World Congress of Psychiatry (Aug. 6, 1999), vol. 2,00.126.
Reis et al. Craving decrease with topiramate in outpatient treatment for cocaine dependence: an open label trial, Rev Bras Psiquiatr 2008;30(2):132-5.
Rogawski et al., Nature Reviews Neuroscience, vol. 5 (1), 2004, pp. 553-564.
Rost et al., The effect of tramadol and other analgesics on the pain . . . , Abstract, Arzneim-Forsch. 1978, vol. 28 (1a0 pp. 181-183).
Rouillon, F., Eur. Neuropsychopharmacol 1999, 9 Suppl. 3, S87-S92.
Rygula et al., "Anhedonia and motivational deficits in rats: Impact of chronic social stress", Behavioral Brain Research, 162 (2005) 127-134.
Sanacora, G. et al., "Impairment of GAB Aergic transmission in depression: New Insights from neuroimaging studies", Critical Reviews in Neurobiology, (2000) 14/1 pp. 23-45, XP001029967, whole document.
Silberstein et al., "Migraine & Epilepsy", www.myepilepsy.com, 2002.
Sofuoglu et al., CNS Drugs 2005: 19(1), pp. 13-25.
Soledade et al.: "Toward the control of Leptosphaeria maculans Design, Synthesis, biological activity, and metabolism of potential detoxification inhibitors of the crucifer phytoalexin brassinin". Bioorganic & Medicinal Chemistry, vol. 14, No. 14, Apr. 17, 2006, pp. 4958-4979, XP005458688.
Stephen, Linda J. et al., "Lamotrigine and topiramate may be a useful combination", The Lancet, vol. 351, No. 9107, pp. 958-959, 1998.
Stephen, Linda J. et al., "Topiramate in Refractory Epilepsy: A Prospective Observational Study", Epilepsia, vol. 41, No. 8, pp. 977-980, 2000.
Stoll et al., Harvard Rev. Psychiatry, Jul./Aug. 1996, vol. 4, No. 2, 77-89.
Storey et al, "Topiramate in Migraine Prevention: A Double Blind, Placebo-Controlled Study", 2001, Headache, 41, pp. 968-975.
Ten Have, R. et al.:"Novel Synthesis of 4(5)-monosubstituted imidazoles via cycloaddition of tosylmethyl isocyanide to aldimines". Tetrahedron, vol. 53, No. 33, Aug. 18, 1997, pp. 11355-11368, XP004106007.
The Merck Manual (1987), Merck Sharp & Dohme Research Laboratories, Rahway, NJ XP002144176, pp. 1351-1356.
Topiramate retrieved from STN Database Accession No. 1998:2562 XP002179444 Abstract & R&D Focus Drug News, Jul. 27, 1998.
Traube, W. et al.:"Zur Kenntnis des Sulfamids". Berichte der Deutschen Chemischen Gesellschaft, vol. 56, 1923, pp. 1656-1663, XP002393747.
Uhart et al., Addiction Biology, 14, pp. 43-64, (2009).
Uys et al., CNS Neurol Disord Drug Targets, 7(5), 2008, pp. 482-91.
Van Amerigen et al. Antiepileptic drugs in the treatment of anxiety disorders: Role in Therapy, Drugs, 2004, 64(19), 2199-2220.
Vandi, A., et al.: "Synthesis and Properties of Some N-Substituted Sulphamides", Journal of Organic Chemistry, vol. 26, No. 4, Apr. 1961, pp. 1136-1138, XP002394144.
Von Seggern, Randal L., et al, "Efficacy of Topiramate in Migraine Prophylaxis: A Retrospective Chart Analysis" Headache (2002), (42)804-809.
Wauquier A et al, "Topiramate: A potent anticonvulsant I the Amygdala-Kindled Rat" Epilepsy Research, NJ, Elsevier Science Publishers, Amsterdam, vol. 24, No. 2, Jun. 1, 1996, p. 73-77, XP002042953.
WebMD Medical News Epilepsy Drugs Fights Migraine, 2002, www.webmd.com/migraine-headaches/news/20020923/epilepsydrug-fights-migraine.
Weib, G. et al.: "Herstellung and Reaktionen von N-Monoalkylamidosulfonylchloriden" Liebigs Annalen Der Chemie, vol. 729, Dec. 1969, pp. 40-51, XP002187581.
Wheeler et al., "Topiramate-treated cluster headache", Neurology (Jul. 1999) vol. 53, No. 1 pp. 234-236.

Wheeler S.D., "Antiepileptic Drug therapy in Migraine Headache", Current Treatment Options Neurology, Sep. 2002; 4(5):383-394.
Wheeler, "Significance of migrainouse features in cluster headache", Headache 38/7 pp. 547-551.
Whitehead, C.W. et al.: "Diuretics. II. Alkoxymercuration oby mixed anion sales of mercury". Journal of the American Chemical Society, vol. 80, No. 9, May 5, 1958, pp. 2182-2185, XP002393746.
Williams, Jr., J.W., et al., Ann. Intern. Med. 2000, 132, 743-756.
Winhusen et al. Drug and Alcohol Dependence 91 (207) 131-148 (2007).
Yang Y. et al., "Neuroprotection by delayed administration of topiratmate in rat model of middle cerebral artery embolization", Brain Research, vol. 804, No. 2, 1998, pp. 169-176, XP000921218.
Young, WB et al, "Topiramate: a case series study in migraine prophylaxis" Cephalalgia (2002), (22)659-663.
Ziegler. E., et al.:"Zur Reaktivitat von C=Ndoppelbindungssytemen, VI. Reaktionen mit Sulfonamiden and Sulfamiden". Zeitschrift Fur Naturforschung, vol. 30B, 1975, pp. 951-953, XP008067475.
Alcaraz et al., Org. Lett., 2004, 6(16), pp. 2705-2708.
Beaudoin et al., J. Org. Chem., 2003, 68, pp. 115-119.
Birch et al., J. Med. Chem., 1999, 42, pp. 3342-3355.
Delgado et al., Tet Lett, 1988, 29(3), pp. 3671-3676.
Estave et al., Tet Lett, 2002, 43, pp. 1019-1021.
Gavernet et al., Bioorg & Med Chem., 2007, 15, pp. 5604-4516.
Hedayatullah et al., Phosphorus and Sulfur, 1985, 25(1), pp. 33-38.
Hirayama et al., Bioorg & Med Chem., 2002, 10, pp. 1509-1523.
Kim et al., Tet Lett, 23(14), pp. 1505-1508, (1982).
Kubicki et al., J Mol Struct., 2001, 531(1-3), p. 65-70.
Lee et al., Org. Chem 1990 55(25) pp. 6098-6104.
Muniz et al., SYNLETT, 2005, 1, pp. 149-151.
Nelson et al., J. Med. Chem., 1977, 20(7), pp. 880-885.
Nelson et al., J. Med. Chem., 1979, 22(9), pp. 1125-1127.
Nicolaou et al., Chem. Eur. J., 2004, 10, pp. 5581-5606.
Okada et al., Tet Lett, 2000, 41, pp. 7047-7051.
Park et al., J. Med. Chem., 2002, 45, pp. 5295-5302.
Winum et al., Org. Lett., 2001, 3(14), pp. 2241-2243.
Xu et al., SYNLETT, 2004, 11, pp. 1901-1904.
Zhong et al., J. Comb. Chem., 2004, 6, pp. 556-563.
Chemische Berichte, 1959, 92, pp. 509-513.
Agrawal et al., Bioorganic and Medicinal Chemistry, 11(2003), pp. 5353-5362.
Casini et al., Bioorganic and Medicinal Chemistry Letters, 13(2003), pp. 841-845.
Pasorekova et al., Journal of Enzyme Inhibition and Medicinal Chemistry, Jun. 2004, vol. 19(3), pp. 199-229.
Supuran et al., Curr. Med. Chem.—Cardiovascular and Hematological Agents, 2004, 2, pp. 49-68.
Supuran et al., Curr. Med. Chem.—Imm., Endoc. & Metab Agents, 2001, 1, 61-97.
Supuran et al., Exp. Opin. Ther. Patents, (2000), 10(5), pp. 575-600.
Supuran et al., Exp. Opin. Ther. Patents, (200), 12(2), pp. 217-242, (2000).
Supuran et al., Medicinal Research Reviews, vol. 23, No. 2, pp. 146-189, 2003.
Thakur at al., Bioorganic and Medicinal Chemistry, 12(2004), pp. 789-793.
Office Action mailed Mar. 26, 2008 in U.S. Appl. No. 11/154,443.
Notice of Allowance mailed Dec. 31, 2008 U.S. Appl. No. 11/154,443.
Notice of Allowance dated Jun. 8, 2009 in U.S. Appl. No. 11/154,443.
Notice of Allowance dated Oct. 9, 2009 in U.S. Appl. No. 11/154,443.
Notice of Allowance dated Feb. 9, 2010 in U.S. Appl. No. 11/154,443.
Notice of Allowance dated May 25, 2010 in U.S. Appl. No. 11/154,443.
Office Action mailed Oct. 3, 2007 in U.S. Appl. No. 11/154,386.
Notice of Allowance dated Mar. 6, 2009 in U.S. Appl. No. 11/154,386.
Office Action mailed Jul. 9, 2008 in U.S. Appl. No. 11/154,386.
Notice of Allowance dated Sep. 10, 2009 in U.S. Appl. No. 11/154,386.
Notice of Allowance dated Feb. 23, 2010 in U.S. Appl. No. 11/154,386.
Office Action mailed Apr. 14, 2008 in U.S. Appl. No. 11/209,122.
Notice of Allowance dated Oct. 30, 2008 in U.S. Appl. No. 11/209,122.
Office Action mailed Mar. 20, 2009 in U.S. Appl. No. 11/209,122.
Notice of Allowance dated Sep. 24, 2009 in U.S. Appl. No. 11/209,122.
Notice of Allowance dated Jan. 13, 2010 in U.S. Appl. No. 11/209,122.
Office Action mailed Aug. 17, 2009 in U.S. Appl. No. 11/611,938.
Final Office Action mailed Feb. 25, 2010 in U.S. Appl. No. 11/611,938.
Office Action mailed Sep. 10, 2008 in U.S. Appl. No. 11/406,794.
Notice of Allowance dated Mar. 13, 2009 in U.S. Appl. No. 11/406,794.
Notice of Allowance dated Jul. 17, 2009 in U.S. Appl. No. 11/406,794.
Office Action mailed Nov. 2, 2009 in U.S. Appl. No. 11/406,794.
Notice of Allowance dated Mar. 17, 2010 in U.S. Appl. No. 11/406,794.
Notice of Allowance dated Jul. 1, 2010 in U.S. Appl. No. 11/406,794.
Office Action mailed Nov. 26, 2008 in U.S. Appl. No. 11/612,071.
Final Office Action mailed Jun. 8, 2009 in U.S. Appl. No. 11/612,071.
Final Office Action mailed Oct. 29, 2009 in U.S. Appl. No. 11/612,146.
Final Office Action mailed Aug. 5, 2008 in U.S. Appl. No. 11/612,146.
Office Action mailed Jan. 29, 2009 in U.S. Appl. No. 11/612,174.
Office Action mailed Mar. 30, 2009 in U.S. Appl. No. 11/612,202.
Office Action mailed Jan. 14, 2010 in U.S. Appl. No. 11/612,202.
Office Action mailed Jul. 21, 2009 in U.S. Appl. No. 11/612,249.
Final Office Action mailed Jan. 28, 2010 in U.S. Appl. No. 11/612,249.
Office Action mailed May 21, 2008 in U.S. Appl. No. 11/674,021.
Final Office Action mailed Jul. 31, 2009 in U.S. Appl. No. 11/674,021.
Notice of Allowance mailed Jun. 16, 2010 in U.S. Appl. No. 11/674,021.
Office Action mailed Apr. 29, 2009 in U.S. Appl. No. 11/750,600.
Final Office Action mailed Dec. 16, 2009 in U.S. Appl. No. 11/750,600.
Final Office Action mailed Mar. 11, 2010 in U.S. Appl. No. 11/750,600.
Notice of Allowance mailed May 28, 2010 in U.S. Appl. No. 11/750,600.
Office Action mailed Jun. 24, 2009 in U.S. Appl. No. 12/055,433.
Final Office Action mailed Feb. 23, 2010 in U.S. Appl. No. 12/055,433.
Office Action dated Jun. 1, 2010 in U.S. Appl. No. 12/488,079.
Aron et al., Neuropharmacology, 10, 459-469, 1971.
Behl et al., Endocrinology, vol. 138, No. 1, pp. 101-106, 1997.
Cleeves et al., "Trazodone is ineffective in essential tremor", J. Neurol Nerusurg Psychiatry, 1990, 53:268-269.
Coyle et al., Science, vol. 262, Issue 5134, pp. 689-695, 1993.
Desagher et al., The Journal of Neuroscience, 1996, 16(8), pp. 2553-2562.
Handley and Mithani, Naunyn. Schmied. Arch. Pharmacol., 327, 1-5, 1984.
Koller et al., "Essential Tremor Variants: Effect of Treatment", abstract, Clinical Pharmacology, 1987.
Merck Manuals Online Medical Library, www.merck.com, 2007.
New England Journal of Medicine, vol. 342:505-507, 2001.
Nickel et al., Journal of Affective Disorders, vol. 87(2-3), 2005, pp. 243-252.
Robinson et al. "Pregablin not Effective for Essential Tremor", www.medpagetoday.com, 2009.
Tabner et al., The Journal of Biological Chemistry, vol. 280, No. 43, pp. 35789-35792, Oct. 28, 2005.
Taylor et al., Science, vol. 296, pp. 1991-1995 (2002).
Notice of Allowance dated Sep. 20, 2010 in U.S. Appl. No. 11/154,443.
Office Action mailed Jul. 29, 2010 in U.S. Appl. No. 11/612,202.
Office Action mailed Jul. 9, 2010 in U.S. Appl. No. 11/612,222.

Notice of Allowance dated Jan. 25, 2011 in U.S. Appl. No. 11/154,443.
Notice of Allowance dated Oct. 22, 2010 in U.S. Appl. No. 11/154,386.
Notice of Allowance dated Jan. 11, 2011 in U.S. Appl. No. 11/209,122.
Notice of Allowance dated Nov. 29, 2010 in U.S. Appl. No. 11/406,794.
Office Action mailed Nov. 15, 2010 in U.S. Appl. No. 11/612,202.
Office Action mailed Oct. 15, 2010 in U.S. Appl. No. 11/612,249.
Notice of Allowance mailed Dec. 15, 2010 in U.S. Appl. No. 11/674,021.
Notice of Allowance mailed Dec. 15, 2010 in U.S. Appl. No. 11/750,600.
Office Action mailed Sep. 22, 2010 in U.S. Appl. No. 12/055,433.
Office Action mailed Nov. 15, 2010 in U.S. Appl. No. 12/055,924.
Notice of Allowance mailed Dec. 14, 2010 in U.S. Appl. No. 12/488,079.
Meert et al., *Pharmacol. Biochem. Behav.*; 2005, 80(2), pp. 309-326.
MacDonald et al., CNS Drugs, 2002, 16(8): 549-562.
Walden et al., Neuropsychobiology, 1998,38: 181-84.
Notice of Allowance dated May 4, 2011 in U.S. Appl. No. 11/154,443.
Notice of Allowance dated Mar. 14, 2011 in U.S. Appl. No. 11/406,794.
Notice of Allowance dated Mar. 14, 2011 in U.S. Appl. No. 11/611,961.
Notice of Allowance dated Mar. 4, 2011 in U.S. Appl. No. 11/612,202.
Office Action mailed Apr. 12, 2011 in U.S. Appl. No. 11/612,222.
Office Action mailed Apr. 22, 2011 in U.S. Appl. No. 11/612,249.
Office Action mailed Jun. 8, 2011 in U.S. Appl. No. 12/055,433.
Office Action mailed May 26, 2011 in U.S. Appl. No. 12/055,695.
Notice of Allowance dated Jun. 1, 2011 in U.S. Appl. No. 11/209,122.
Notice of Allowance dated Aug. 12, 2011 in U.S. Appl. No. 11/154,443.
Notice of Allowance dated Jun. 30, 2011 in U.S. Appl. No. 11/406,794.
Notice of Allowance dated Oct. 4, 2011 in U.S. Appl. No. 11/406,794.
Corrected Notice of Allowance dated Jul. 20, 2011 in U.S. Appl. No. 11/406,794.
Office Action mailed Jul. 11, 2011 in U.S. Appl. No. 12/431,141.
Notice of Allowance dated Sep. 19, 2011 in U.S. Appl. No. 11/612,202.
Office Action mailed Oct. 4, 2011 in U.S. Appl. No. 10/612,222.
Office Action mailed Oct. 6, 2011 in U.S. Appl. No. 10/612,249.
Notice of Allowance dated Aug. 22, 2011 in U.S. Appl. No. 11/674,021.
Office Action/Interview Summary dated Sep. 1, 2011 in U.S. Appl. No. 11/750,600.
Notice of Allowance dated Sep. 12, 2011 in U.S. Appl. No. 11/750,600.
Office Action mailed Jul. 15, 2011 in U.S. Appl. No. 12/055,695.
Notice of Allowance mailed Apr. 12, 2011 in U.S. Appl. No. 12/055,924.
Office Action mailed Oct. 6, 2011 in U.S. Appl. No. 12/349,184.
Notice of Allowance dated Jun. 21, 2011 in U.S. Appl. No. 12/488,079.
Office Action mailed Jul. 8, 2011 in U.S. Appl. No. 12/502,472.
Bernando, L., Prevention of epilepsy after head trauma: do we need drugs or a new approach?, 2003, Epilepsia, 44, (Suppl. 10), 27-33.
Byrn et al., Pharmaceutical Research, Kluwer Academic Publishers, New York, NY, US, vol. 12, No. 7, 1995, pp. 945-954.
D'Ambrosio et al., Curr. Opin. Neurol. Dec. 2004; 17(6): 731-735.
Jones et al. "Screening for Major Depression in Epilepsy with Common Self-Report Depression Inventories", Epilepsia, May 2005; 46(5):731-735.
Kane et al., Psychopharmacological Bulletin, vol. 24, pp. 62-67 (1988).
Kaplan & Sadock's Comprehensive Textbook of Psychiatry, Seventh Edition, vol. II, Lippincott Williams & Wilkins: Philadelphia, pp. 2467-2468, 2000.
Kaplan & Sadock's Comprehensive Textbook of Psychiatry, Seventh Edition, vol. II, Lippincott Williams & Wilkins: Philadelphia, pp. 2470-2471, 2000.
Physician's Desk Reference; Kaplan & Sadock's Comprehensive Textbook of Psychiatry, Seventh Edition, vol. II, Lippincott Williams & Wilkins: Philadelphia, pp. 2466-2467, 2000 (olanzapine).
Physician's Desk Reference; Kaplan & Sadock's Comprehensive Textbook of Psychiatry, Seventh Edition, vol. II, Lippincott Williams & Wilkins: Philadelphia, pp. 2456-2463, 2000 (clozapine).
Physician's Desk Reference; Kaplan & Sadock's Comprehensive Textbook of Psychiatry, Seventh Edition, vol. II, Lippincott Williams & Wilkins: Philadelphia, pp. 2463-2466, 2000 (risperidone).
Physician's Desk Reference; Kaplan & Sadock's Comprehensive Textbook of Psychiatry, Seventh Edition, vol. II, Lippincott Williams & Wilkins: Philadelphia, pp. 2469-2470, 2000 (quetiapine).
Sullivan, P., Epilepsy & Behavior 7 (2005) S12-S17.
Notice of Allowance dated Jan. 17, 2012 in U.S. Appl. No. 11/406,794.
Notice of Allowance dated Dec. 22, 2011 in U.S. Appl. No. 11/750,600.
Office Action mailed Dec. 22, 2011 in U.S. Appl. No. 12/055,433.
Office Action mailed Nov. 21, 2011 in U.S. Appl. No. 12/055,695.
Notice of Allowance dated Nov. 1, 2011 in U.S. Appl. No. 12/488,079.
Notice of Allowance mailed Nov. 28, 2011 in U.S. Appl. No. 12/502,472.
International Search Report re: PCT/US2006/048477 dated Aug. 8, 2007.
Brodie, M.S.; Pesold, C; Appel, S.B. Alcohol Clin Exp Res 1999, 23, pp. 1848-1852.
Krampfl et al., The European Journal of Neuroscience; vol. 22, Issue: 1, pp. 10-20, 2005.
Scimemi et al., The Journal of Neuroscience: the official journal of Society for Neuroscience; vol. 25; Issue: 43, pp. 10016-10024, 2005.
Wise RA, Drug Alcohol Depend, 1998, 51, pp. 13-22.
Wise RA, NIDA Res Mono, 1984, 50, pp. 15-33.
Notice of Allowance dated Oct. 18, 2011 in U.S. Appl. No. 11/209,122.
Notice of Allowance dated Mar. 20, 2012 in U.S. Appl. No. 11/209,122.
Notice of Allowance mailed Oct. 11, 2011 in U.S. Appl. No. 11/612,071.
Notice of Allowance mailed Mar. 9, 2012 in U.S. Appl. No. 11/612,071.
Notice of Allowance mailed Apr. 25, 2012 in U.S. Appl. No. 11/612,146.
Final Office Action dated Dec. 15, 2011 in U.S. Appl. No. 12/431,141.
Interview Summary dated Mar. 26, 2012 in U.S. Appl. No. 12/431,141.
Notice of Allowance mailed Jan. 4, 2012 in U.S. Appl. No. 11/612,202.
Notice of Allowance mailed Apr. 16, 2012 in U.S. Appl. No. 11/612,202.
Office Action dated Mar. 30, 2012 in U.S. Appl. No. 11/750,600.
Interview Summary dated Apr. 4, 2012 in U.S. Appl. No. 12/055,433.
Notice of Allowance dated Mar. 1, 2012 in U.S. Appl. No. 12/488,079.
Notice of Allowance dated Mar. 28, 1012 in U.S. Appl. No. 12/502,472.
Notice of Allowance dated Jul. 19, 2012 in U.S. Appl. No. 11/154,386.
Notice of Allowance mailed May 10, 2012 in U.S. Appl. No. 11/406,794.
Notice of Allowance mailed May 11, 2012 in U.S. Appl. No. 13/301,109.
Notice of Allowance mailed May 11, 2012 in U.S. Appl. No. 12/349,184.
Notice of Allowance mailed Jun. 18, 2012 in U.S. Appl. No. 12/488,079.
Notice of Allowance mailed Jul. 16, 2012 in U.S. Appl. No. 12/502,472.
Brandt et al., Neuropsychobiology, 1998,38, pp. 202 to 203.

Dib, Jean G., Current Medical Research and Opinion, 2004, 20, 12, p. 1857-1861.
Edeh et al, (1987) Relationship between interictal psychopathology and the type of epilepsy. Results of a survey in general practice. Br J Psychiatry 151:95-101.
Ettinger et al., (2004) Depression and comorbidity in community-based patients with epilepsy or asthma. Neurology 63:1008-1014.
Forsgren et al., (1990) An incident case-referent study of epileptic seizures in adults. Epilepsy Res 6:66-81.
Hesdorffer et al. (2006) Depression and suicide attempt as risk factors for incident unprovoked seizures. Ann Neurol 59:35-41.
Hesdorffer et al. (2000) Major depression is a risk factor for seizures in older adults. Ann Neurol 47:246-249.
Jacoby et al. (1996) The clinical course of epilepsy and its psychosocial correlates: findings from a U.K. Community study. Epilepsia 37:148-161.
Kanner, Am., (2006) Epilepsy, suicidal behaviour, and depression: do they share common pathogenic mechanisms? Lancet Neurol 5:107-108.
Ottman et al., Epilepsia, 52(2):308-315, 2011.
Tanimukai et al., International Pharmacopsychiatry, 1970, vol. 5, No. 1, pp. 35 to 43.
Thienel et al., Acta Neurologica Scandinavica, 2004, 110, 4, p. 221-231.
Harwood, AJ, Molecular Psychiatry (2005) 10,117-126.
Keck et al., J. Clin. Psychiatry, 2002, 63 (suppl 4).
Notice of Allowance mailed Aug. 9, 2012 in U.S. Appl. No. 11/612,202.
Final Office Action mailed Sep. 10, 2012 in U.S. Appl. No. 11/750,600.
Notice of Allowance mailed Oct. 10, 2012 in U.S. Appl. No. 12/488,079.
Notice of Allowance dated Nov. 20, 2012 in U.S. Appl. No. 11/154,386.
Notice of Allowance mailed Dec. 24, 2012 in U.S. Appl. No. 11/611,938.
Notice of Allowance mailed Jan. 22, 2013 in U.S. Appl. No. 11/612,071.
Notice of Allowance mailed Nov. 26, 2012 in U.S. Appl. No. 11/612,202.
Notice of Allowance mailed Feb. 7, 2013 2012 in U.S. Appl. No. 12/488,079.
Benjamin et al. J Biomol Screening, 2006, vol. 11, pp. 29-39.
Brown et al. Tetrahedron, 1987, vol. 43, pp. 4071-4078.
Dunham et al. J Am Pharm Assoc Sci Ed, 1957, vol. 46, pp. 208-209.
Ettinger et al. Neurotherapeutics, 2007, vol. 4, pp. 75-83.
Gavernet et al. Bioorg Med Chem 2007, vol. 15, pp. 1556-1567.
Gavernet et al. J Med Chem, 2009, vol. 52, pp. 1592-1601.
Gribkoff, V., Expert Opin Ther Pat., 2003 vol. 7, pp. 737-748.
Kohling, R., Epilepsia, 2002, vol. 43, pp. 1278-1295.
Kuzimski et al., Epilepsia, 2005, vol. 46, pp. 481-489.
Landmark, C., CNS Drugs, 2008, vol. 22, pp. 27-47.
Liu et al., Epilepsy Res, 2006, vol. 70, pp. 263-268.
Liu et al., Neuropharmacology, 2003, vol. 44, pp. 413-422.
Lombardo et al., Mol Brain Res, 1996, vol. 35, pp. 84-90.
Lothman et al., Epilepsy Res, 1988, vol. 2, pp. 356-366.
Lothman et al., Epilepsy Res, 1988, vol. 2, pp. 367-379.
Lukyanetz et al., Epilepsia, 2002, vol. 43, pp. 9-18.
Maryanoff et al, Drugs Future, 1989, vol. 14, pp. 342-344.
Maryanoff et al, J Med Chem, 2008, vol. 51, pp. 2518-2521.
Maryanoff et al., Curr Top Med Chem, 2009, vol. 9, pp. 1049-1062.
Maryanoff, B., J Med Chem, 2009, vol. 52, pp. 3431-3440.
Orloff et al., Proc Soc Exp Biol Med, 1949, vol. 70, pp. 254-257.
Parker et al., J Med Chem, 2009, vol. 52, pp. 7528-7536.
Remington's The Science and Practice of Pharmacy, $19^{th}$ Edition, Published 1998, vol. I, pp. 371-375.
Rogawski et al., Nat Med, 2004, vol. 10, pp. 685-692.
Rogawski, M., Epilepsy Res, 2006, vol. 69, pp. 273-294.
Shank et al., CNS Neurosci Ther, 2008, vol. 14, pp. 120-142.
Shank et al., Epilepsia, 1994, vol. 35, pp. 450-460.
Shank et al., J Enzym Inh Med Chem, 2008, vol. 23, pp. 271-276.
Shingles et al., Anal Biochem, 1997, vol. 252, pp. 190-197.
Soderpalm, B., Eur J Pain, 2002, vol. 6, Suppl A, p. 3-9.
Stella et al., Drugs, 29: 455-473 (1985).
Swinyard et al., J Pharmacol Exp Ther, 1952, vol. 106, pp. 319-330.
Swinyard, E., Epilepsia, 1969, vol. 10, pp. 107-119.
Wang et al., Science, 1998 vol. 282, pp. 1890-1893.
White et al., Antiepileptic Drugs, 5th Ed., 2002, pp. 36-48.
White et al., Epilepsy Res, 1992, vol. 12, pp. 217-226.
White et al., Int Rev Neurobiol, 2007, vol. 81, pp. 85-110.
Winum et al., Expert Opin Ther Pat, 2006, vol. 16, pp. 27-47.
Zaremba et al., Pharmacol Rep, 2006, vol. 58, pp. 1-12.

USE OF BENZO-FUSED HETEROCYCLE SULFAMIDE DERIVATIVES FOR LOWERING LIPIDS AND LOWERING BLOOD GLUCOSE LEVELS

CROSS REFERENCE TO RELATED APPLICATIONS

This application claims the benefit of U.S. Provisional Application 60/751,677, filed on Dec. 19, 2005, which is incorporated by reference herein in its entirety.

FIELD OF THE INVENTION

The present invention is directed to the use of benzo-fused heterocycle sulfamide derivatives for lowering lipids, lowering blood glucose levels, improving glycemic control, treating Type II diabetes mellitis, metabolic syndrome, hyperglycemia and related disorders.

BACKGROUND OF THE INVENTION

Diabetes mellitus is a medical term for the presence of elevated blood glucose. People with diabetes either don't produce insulin, produce too little insulin or do not respond to insulin, resulting in the build up of glucose in the blood. The most common form of diabetes is Type 2 diabetes, once referred to as adult onset diabetes or non-insulin dependent diabetes (NIDDM), which may account for >90% of diabetes in adults. However, as the younger population becomes increasingly overweight or obese, Type 2 diabetes is becoming more prevalent in teens and children. Diabetes may also refer to gestational diabetes, Type 1 diabetes or autoimmune diabetes, once referred to as juvenile onset diabetes and type 1½ diabetes, also referred to as latent-autoimmune diabetes in adults or LADA. Diabetes may occur because of poor dietary habits or lack of physical activity (e.g., sedentary lifestyle), genetic mutations, injury to the pancreas, drug (e.g., AIDS therapies) or chemical (e.g., steroid) exposure or disease (e.g., cystic fibrosis, Down syndrome, Cushing's syndrome). Two rare types of genetic defects leading to diabetes are termed maturity-onset diabetes of the young (MODY) and atypical diabetes mellitus (ADM).

Type II diabetes mellitus (non-insulin-dependent diabetes mellitus or NIDDM) is a metabolic disorder involving dis-regulation of glucose metabolism and insulin resistance, and long-term complications involving the eyes, kidneys, nerves, and blood vessels. Type II diabetes mellitus usually develops in adulthood (middle life or later) and is described as the body's inability to make either sufficient insulin (abnormal insulin secretion) or its inability to effectively use insulin (resistance to insulin action in target organs and tissues). More particularly, patients suffering from Type II diabetes mellitus have a relative insulin deficiency. That is, in these patients, plasma insulin levels are normal to high in absolute terms, although they are lower than predicted for the level of plasma glucose that is present.

Type II diabetes mellitus is characterized by the following clinical signs or symptoms: persistently elevated plasma glucose concentration or hyperglycemia; polyuria; polydipsia and/or polyphagia; chronic microvascular complications such as retinopathy, nephropathy and neuropathy; and macrovascular complications such as hyperlipidemia and hypertension which can lead to blindness, end-stage renal disease, limb amputation and myocardial infarction.

Syndrome X, also termed Insulin Resistance Syndrome (IRS), Metabolic Syndrome, or Metabolic Syndrome X, is a disorder that presents risk factors for the development of Type II diabetes mellitus and cardiovascular disease including glucose intolerance, hyperinsulinemia and insulin resistance, hypertriglyceridemia, hypertension and obesity.

The diagnosis of Type II diabetes mellitus includes assessment of symptoms and measurement of glucose in the urine and blood. Blood glucose level determination is necessary for an accurate diagnosis. More specifically, fasting blood glucose level determination is a standard approach used. However, the oral glucose tolerance test (OGTT) is considered to be more sensitive than fasted blood glucose level. Type II diabetes mellitus is associated with impaired oral glucose tolerance (OGT). The OGTT thus can aid in the diagnosis of Type II diabetes mellitus, although generally not necessary for the diagnosis of diabetes (Emancipator K, Am J Clin Pathol 1999 November;112(5):665-74; Type 2 Diabetes Mellitus, Decision Resources Inc., March 2000). The OGTT allows for an estimation of pancreatic beta-cell secretory function and insulin sensitivity, which helps in the diagnosis of Type II diabetes mellitus and evaluation of the severity or progression of the disease (e.g., Caumo A, Bergman R N, Cobelli C,. J Clin Endocrinol Metab 2000, 85(11):4396-402). More particularly, the OGTT is extremely helpful in establishing the degree of hyperglycemia in patients with multiple borderline fasting blood glucose levels that have not been diagnosed as diabetics. In addition, the OGTT is useful in testing patients with symptoms of Type II diabetes mellitus where the possible diagnosis of abnormal carbohydrate metabolism has to be clearly established or refuted.

Thus, impaired glucose tolerance is diagnosed in individuals that have fasting blood glucose levels less than those required for a diagnosis of Type II diabetes mellitus, but have a plasma glucose response during the OGTT between normal and diabetics. Impaired glucose tolerance is considered a prediabetic condition, and impaired glucose tolerance (as defined by the OGTT) is a strong predictor for the development of Type II diabetes mellitus (Haffner S M, Diabet Med 1997 August;14 Suppl 3:S12-8).

Type II diabetes mellitus is a progressive disease associated with the reduction of pancreatic function and/or other insulin-related processes, aggravated by increased plasma glucose levels. Thus, Type II diabetes mellitus usually has a prolonged prediabetic phase and various pathophysiological mechanisms can lead to pathological hyperglycemia and impaired glucose tolerance, for instance, abnormalities in glucose utilization and effectiveness, insulin action and/or insulin production in the prediabetic state (Goldberg R B, Med Clin North Am 1998 July;82(4):805-21).

The prediabetic state associated with glucose intolerance can also be associated with a predisposition to abdominal obesity, insulin resistance, hyperlipidemia, and high blood pressure, that is, Syndrome X (Groop L, Forsblom C, Lehtovirta M, Am J Hypertens 1997 September;10(9 Pt 2):172S-180S; Haffner S M, J Diabetes Complications 1997 March-April;11(2):69-76; Beck-Nielsen H, Henriksen J E, Alford F, Hother-Nielson O, Diabet Med 1996 September;13(9 Suppl 6):S78-84).

Thus, defective carbohydrate metabolism is pivotal to the pathogenesis of Type II diabetes mellitus and impaired glucose tolerance (Dinneen S F, Diabet Med 1997 August;14 Suppl 3:S19-24). In fact, a continuum from impaired glucose tolerance and impaired fasting glucose to definitive Type II diabetes mellitus exists (Ramlo-Halsted B A, Edelman S V, Prim Care 1999 December;26(4):771-89).

Early intervention in individuals at risk to develop Type II diabetes mellitus, focusing on reducing the pathological hyperglycemia or impaired glucose tolerance may prevent or delay the progression towards Type II diabetes mellitus and associated complications and/or Syndrome X. Therefore, by effectively treating impaired oral glucose tolerance and/or elevated blood glucose levels, one can prevent or inhibit the progression of the disorder to Type II diabetes mellitus or Syndrome X.

Dyslipidemia is a group of diseases characterized by abnormal changes or levels in concentrations of lipoproteins and associated lipids, such as triglyceride and cholesterol, in the blood. Lipids are transported through the bloodstream in the form of lipoproteins consisting essentially of a core of apolar molecules such as triglyceride and cholesterol ester surrounded by an envelope of amphipathic lipids, primarily phospholipids. Acquired hyperlipidemia/hyperlipoproteinemia develops as a consequence of dietary imbalance, drug or compound effects, or disease, such as thyroid deficiency or diabetes. Familial hyperlipidemia/hyperlipoproteinemia is characterized by autosomal inheritance and is associated with an increase in lipoprotein and lipid content in the blood. Familial hyperlipidemia/hyperlipoproteinemia is subdivided into to five categories (types I-V) depending on the composition and type of lipoprotein particles in the blood. For example, in Type I and Type IV hyperlipoproteinemia, triglyceride is elevated predominately in chylomicron and VLDL particles, respectively. In general, there is an inverse relation between HDL-cholesterol and triglyceride levels that contributes to dyslipidemia. If left untreated, dyslipidemia (e.g., low HDL-cholesterol and high triglyceride or LDL-cholesterol levels) can exacerbate other conditions, such as pancreatitis, abnormal glucose tolerance, diabetes, coronary artery disease, ischemic heart diseases, atherosclerosis, hepatosplenomegaly, and fatty liver disease.

There remains a need to provide an effective treatment for glucose related disorders such as elevated glucose levels, Type II diabetes mellitus, Syndrome X, and the like. There also remains need to provide an effective treatment for lipid related disorders such as elevated glucose levels, dyslipidemia, and the like.

SUMMARY OF THE INVENTION

The present invention is directed to a method for the treatment of glucose related disorders and/or lipid related disorders comprising administering to a subject in need thereof a therapeutically effective amount of a compound of formula (I)

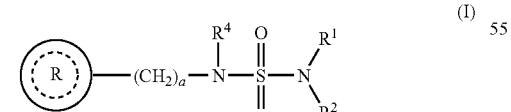

(I)

wherein $R^1$ and $R^2$ are each independently selected from the group consisting of hydrogen and lower alkyl;

$R^4$ is selected from the group consisting of hydrogen and lower alkyl;

a is an integer from 1 to 2;

is selected from the group consisting of

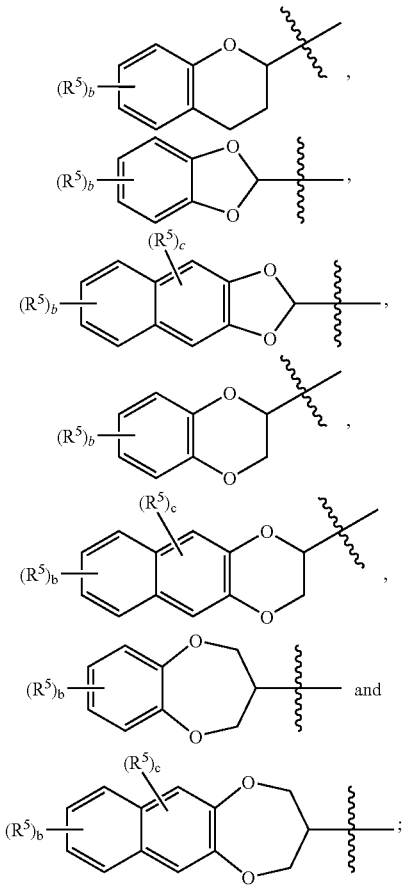

wherein b is an integer from 0 to 4; and wherein c is an integer from 0 to 2;

each $R^5$ is independently selected from the group consisting of halogen, lower alkyl and nitro;

provided that when

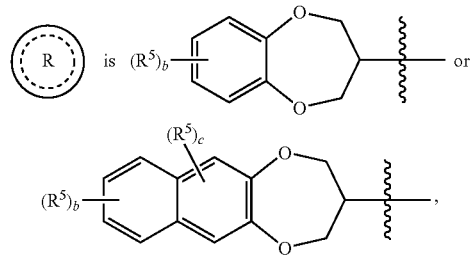

then a is 1;

or a pharmaceutically acceptable salt thereof.

The present invention is further directed to a method for the treatment of glucose related disorders and/or lipid related disorders comprising administering to a subject in need thereof a therapeutically effective amount of compound of formula (II)

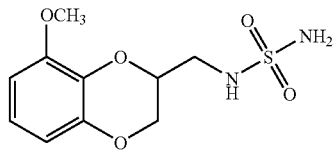

or a pharmaceutically acceptable salt thereof.

Exemplifying the invention is a method of treating glucose related disorders comprising administering to a subject in need thereof a therapeutically effective amount of any of the compounds described above. In another example, the invention is directed to a method of treating lipid related disorders comprising administering to a subject in need thereof a therapeutically effective amount of any of the compounds described above.

The present invention is further directed to a method for the treatment of a glucose related disorder comprising co-therapy with at least one anti-diabetic agent and a compound of formula (I) or formula (II) as described herein. The present invention is further directed to a method for the treatment of a lipid related disorder comprising co-therapy with at least one anti-lipid agent and a compound of formula (I) or formula (II) as described herein. The present invention is further directed to a method for the treatment of a glucose related disorder or a lipid-related disorder comprising co-therapy with at least one anti-diabetic agent and/or at least one anti-lipid agent and a compound of formula (I) or formula (II) as described herein. The present invention is further directed to a method for the treatment of a glucose-related disorder comprising co-therapy with an anti-obesity agent and a compound of formula (I) or formula (II) as described herein.

DETAILED DESCRIPTION OF THE INVENTION

The present invention is directed to a method for the treatment of glucose related disorders and/or lipid related disorders comprising administering to a subject in need thereof a therapeutically effective amount of a compound of formula (I)

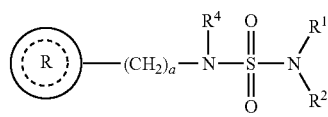

or a pharmaceutically acceptable salt thereof, wherein

a, $R^1$, $R^2$ and $R^4$ are as herein defined.

The present invention is further directed to methods for the treatment of glucose related disorders and lipid related disorders comprising co-therapy with at least one anti-diabetic and/or at least one anti-lipid agent and a compound of formula (I) or formula (II) as described herein.

One skilled in the art will recognize that treatment of glucose related disorders and/or lipid-related disorders may further benefit from treatment of co-morbid overweight and obesity conditions. Thus, in an embodiment, the methods of the present invention comprise co-therapy with an anti-obesity agent and a compound of formula (I) or formula (II) as described herein.

As used herein, the term "glucose related disorder" shall be defined as any disorder which is characterized by elevated glucose levels. Glucose related disorders include elevated glucose level, pre-diabetes, impaired oral glucose tolerance, poor glycemic control, Type II Diabetes Mellitus, Syndrome X (also known as metabolic syndrome), gestational diabetes, insulin resistance, hyperglycemia and loss of muscle mass as a results of hyperglycemia (cachexia).

Treatment of glucose related disorders may comprise lowering glucose levels, improving glycemic control, decreasing insulin resistance and/or preventing the development of a glucose related disorder (for example preventing a patient suffering from impaired oral glucose tolerance or elevated glucose levels from developing Type II diabetes mellitus).

As used herein, the term "lipid related disorder" shall be defined as any disorder which is characterized by non-normal lipid levels. Lipid related disorders include elevated triglyceride levels, low HDL cholesterol and dyslipidemia, preferably elevated triglyceride levels or low HDL cholesterol levels Treatment of lipid related disorder may comprise lowering triglycerides, elevating HDL cholesterol and/or improving the triglyceride/HDL ratio.

As used herein, the term "anti-diabetic agent" shall mean any pharmaceutical agent which decreases blood levels, improves glycemic control and/or improves insulin sensitivity. Anti-diabetic agents useful for the treatment of Type II diabetes mellitus and Syndrome X include, but are not limited to, sulfonylureas, meglitinides, agents which modify insulin secretion, biguanides, thiazolidinediones, PPAR-gamma agonists, Retinoid-X receptor (RXR) modulators, insulin sensitizing agents, alpha-glucosidase inhibitors, insulins, small molecule mimics of insulin, Na-glucose co-transporter inhibitors, amylin agonists, glucagon antagonists, GLP-1 and GLP-1 analogs, DPPIV inhibitors, and the like.

Suitable examples of anti-diabetic agents include, exenatide, chlorpropamide, tolazamide, tolbutamide, glyburide, glipizide, glimepiride, repaglinide, metformin, rosiglitazone, pioglitazone, troglitazone, isaglitazone (known as MCC-555), 2-[2-[(2R)-4-hexyl-3,4-dihydro-3-oxo-2H-1,4-benzoxazin-2-yl]ethoxy]-benzene acetic acid, GW2570, targretin, 9-cis-retinoic acid, ascarbose, miglitol, L-783281, TE-17411, T-1095, BAY-279955, phlorizen, pramlintide, regular-acting insulin, short-acting insulin, intermediate-acting insulin, long-acting insulin, inhaled insulin, insulin analogues, acetohexamide, buformin, glibornuride, glyhexamide, glymidine, linogliride, palmoxirate, zopolrestat; etoformin, gllicalzide, glypinamide, and the like.

More particularly, anti-diabetic agents include, but are not limited to:

(a) Sulfonylureas, which increase insulin production by stimulating pancreatic beta cells, and therefore act as insulin secretagogues. The primary mechanism of action of sulfonylureas is to close ATP-sensitive potassium channels in the beta-cell plasma membrane, initiating a chain of events that result in insulin release. Suitable examples of sulfonylureas include, but are not limited to chlorpropamide, tolazamide, tolbutamide, glyburide, glipizide, glimepiride, and like;

(b) Meglitinides, another class of insulin secretagogues, that have a mechanism of action distinct from that of the sulfonylureas. Suitable examples of meglitinides include, but are not limited to repaglinide;

(c) Agents which modify insulin secretion such as Glucagon-like Peptide-1(GLP-1) and it's mimetics, Glucose-insulinotropic peptide (GIP) and it's mimetics, Exendin and it's mimetics, and Dipeptyl Protease Inhibitors (DPPIV);

(d) Biguanides which decrease liver glucose production and increase the uptake of glucose. Suitable examples include, but are not limited to metformin;

(e) Thiazolidinediones, insulin sensitizing drugs which decrease peripheral insulin resistance by enhancing the effects of insulin at target organs and tissues. These drugs bind and activate the nuclear receptor, peroxisome proliferator-activated receptor-gamma (PPAR-gamma) which increases transcription of specific insulin-responsive genes. Suitable examples of PPAR-gamma agonists are the thiazolidinediones which include, but are not limited to rosiglitazone, pioglitazone, troglitazone, isaglitazone (known as MCC-555), 2-[2-[(2R)-4-hexyl-3,4-dihydro-3-oxo-2H-1,4-benzoxazin-2-yl]ethoxy]-benzene acetic acid, and the like. Additionally, the non-thiazolidinediones also act as insulin sensitizing drugs, and include, but are not limited to GW2570, and the like;

(f) Retinoid-X receptor (RXR) modulators, also insulin sensitizing drugs, which include, but are not limited to targretin, 9-cis-retinoic acid, and the like;

(g) Other insulin sensitizing agents include, but are not limited to INS-1, PTP-1B inhibitors, GSK3 inhibitors, glycogen phosphorylase a inhibitors, fructose-1,6-bisphosphatase inhibitors, and the like;

(h) Alpha-glucosidase inhibitors which act to inhibit alpha-glucosidase. Alpha-glucosidase converts fructose to glucose, thus these inhibitors delay the digestion of carbohydrates. The undigested carbohydrates are subsequently broken down in the gut, thereby reducing the post-prandial glucose peak. Suitable examples include, but are not limited to, acarbose and miglitol;

(i) Insulins, including regular or short-acting, intermediate-acting, and long-acting insulins, inhaled insulin and insulin analogues such as insulin molecules with minor differences in the natural amino acid sequence. These modified insulins may have faster onset of action and/or shorter duration of action;

(j) Small molecule mimics of insulin, including, but not limited to L-783281, TE-17411, and the like;

(k) Na-glucose co-transporter inhibitors which inhibit the renal reabsorption of glucose such as T-1095, T-1095A, phlorizen, and the like;

(l) Amylin agonists which include, but are not limited to pramlintide, and the like; and (k) Glucagon antagonists such as AY-279955, and the like.

As used herein, unless otherwise noted, the term "anti-lipid agent" shall mean any pharmaceutical agent capable of lowering triglycerides, lowering lipids, elevating HDL levels or improving the triglyceride/HDL Cholesterol ratio. Suitable examples include, but are not limited to, anti-lipemic agents, bile acid resins, cholesterol absorption inhibitors, fibric acid derivatives, HMG-CoA reductase inhibitors (i.e. statins). Preferable, the anti-lipid agent is a statin selected from the group consisting of atorvastatin (Lipitor), cerivastatin (Baycol), fluvastatin (Lescol), lovastatin, (Mevacor), pravastatin (Pravachol), rosuvastatin (Crestor), simvastatin (Zocor).

As used herein, unless otherwise noted, the term "anti-obesity agent" shall mean any pharmaceutical agent that treats obesity, promotes weight loss and/or suppresses appetite. Suitable examples of weight loss promoting include, but are not limited to rimonabant, orlistat, sibutramine, mazindol, benzphetamine, phenmetrazine, phentermine, diethylpropion, mazindol, phenylpropanolamine, ephedrine, quipazine, fluoxetine, sertraline, fenfluramine, dexfenfluramine, apomorphine, Exendin, dehydroepiandrosterone, etiocholandione, testosterone, oxandrolone, topiramate, and the like. Preferably, the weight loss promoting agent is rimonabant, topiramate, orlistat or sibutramine.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

Wherein the present invention is directed to co-therapy or combination therapy, comprising administration of one or more compound(s) of formula (I) or formula (II) and one or more anti-diabetic and/or anti-lipid agents, "therapeutically effective amount" shall mean that amount of the combination of agents taken together so that the combined effect elicits the desired biological or medicinal response. For example, the therapeutically effective amount of co-therapy comprising administration of a compound of formula (I) or formula (II) and the anti-diabetic and/or anti-lipid agent would be the amount of the compound of formula (I) or formula (II) and the amount of the antidepressant that when taken together or sequentially have a combined effect that is therapeutically effective. Further, it will be recognized by one skilled in the art that in the case of co-therapy with a therapeutically effective amount, as in the example above, the amount of the compound of formula (I) or formula (II) and/or the amount of the anti-diabetic and/or anti-lipid agent individually may or may not be therapeutically effective.

As used herein, the terms "co-therapy" and "combination therapy" shall mean treatment of a subject in need thereof by administering one or more compounds of formula (I) or formula (II) in combination with one or more anti-diabetic and/or anti-lipid agent(s), wherein the compound(s) of formula (I) or formula (II) and the anti-diabetic and/or anti-lipid agent(s) are administered by any suitable means, simultaneously, sequentially, separately or in a single pharmaceutical formulation. Where the compound(s) of formula (I) or formula (II) and the anti-diabetic and/or anti-lipid agent(s) are administered in separate dosage forms, the number of dosages administered per day for each compound may be the same or different. The compound(s) of formula (I) or formula (II) and the anti-diabetic and/or anti-lipid agent(s) may be administered via the same or different routes of administration. Examples of suitable methods of administration include, but are not limited to, oral, intravenous (iv), intramuscular (im), subcutaneous (sc), transdermal, and rectal. Compounds may also be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices. The compound(s) of formula (I) or formula (II) and the anti-diabetic and/or anti-lipid agent(s) may be administered according to simultaneous or alternating regimens, at the same or different times during the course of the therapy, concurrently in divided or single forms.

In an embodiment of the present invention $R^1$ is selected from the group consisting of hydrogen and methyl. In another embodiment of the present invention $R^2$ is selected from the group consisting of hydrogen and methyl. In yet another embodiment of the present invention $R^1$ and $R^2$ are each hydrogen or $R^1$ and $R^2$ are each methyl.

In an embodiment of the present invention —$(CH_2)_a$— is selected from the group consisting of —$CH_2$— and —$CH_2$—$CH_2$—. In another embodiment of the present invention —$(CH_2)_a$— is —$CH_2$—.

In an embodiment of the present $R^4$ is selected from the group consisting of hydrogen and methyl, preferably, $R^4$ is hydrogen.

In an embodiment of the present invention a is 1.

In an embodiment of the present invention b is an integer from 0 to 2. In another embodiment of the present invention c is an integer from 0 to 2. In another embodiment of the present invention b is an integer from 0 to 1. In another embodiment of the present invention c is an integer from 0 to 1. In yet another embodiment of the present invention the sum of b and c is an integer form 0 to 2, preferably an integer form 0 to 1. In yet another embodiment of the present invention b is an integer from 0 to 2 and c is 0.

In an embodiment of the present invention,

is selected from the group consisting of

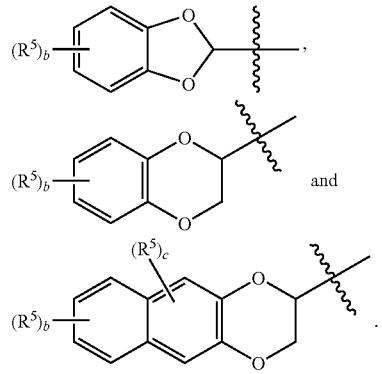

In another embodiment of the present invention,

is selected from the group consisting of

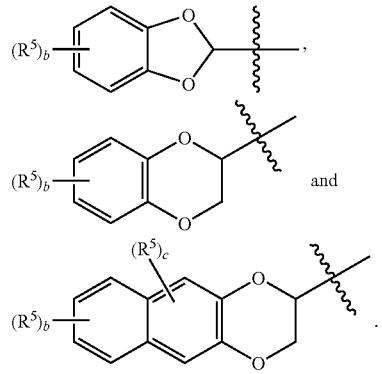

In an embodiment of the present invention,

is selected from the group consisting of 2-(2,3-dihydro-benzo[1,4]dioxinyl), 2-(benzo[1,3]dioxolyl), 3-(3,4-dihydro-benzo[1,4]dioxepinyl), 2-(6-chloro-2,3-dihydro-benzo[1,4]dioxinyl), 2-(6-fluoro-2,3-dihydro-benzo[1,4]dioxinyl), 2-(chromanyl), 2-(5-fluoro-2,3-dihydro-benzo[1,4]dioxinyl), 2-(7-chloro-2,3-dihydro-benzo[1,4]dioxinyl), 2-(6-chloro-benzo[1,3]dioxolyl), 2-(7-nitro-2,3-dihydro-benzo[1,4]dioxinyl), 2-(7-methyl-2,3-dihydro-benzo[1,4]dioxinyl), 2-(5-chloro-2,3-dihydro-benzo[1,4]dioxinyl), 2-(6-bromo-2,3-dihydro-benzo[1,4]dioxinyl), 2-(6,7-dichloro-2,3-dihydro-benzo[1,4]dioxinyl), 2-(8-chloro-2,3-dihydro-benzo[1,4]dioxinyl), 2-(2,3-dihydro-naphtho[2,3-b][1,4]dioxinyl) and 2-(4-methyl-benzo[1,3]dioxolyl).

In another embodiment of the present invention,

is selected from the group consisting 2-(benzo[1,3]dioxolyl), 2-(2,3-dihydro-benzo[1,4]dioxinyl), 2-(6-chloro-2,3-dihydro-benzo[1,4]dioxinyl), 2-(7-chloro-2,3-dihydro-benzo[1,4]dioxinyl), 2-(7-methyl-2,3-dihydro-benzo[1,4]dioxinyl), 2-(6-bromo-2,3-dihydro-benzo[1,4]dioxinyl) and 2-(6,7-dichloro-2,3-dihydro-benzo[1,4]dioxinyl). In another embodiment of the present invention,

is selected from the group consisting of 2-(2,3-dihydro-benzo[1,4]dioxinyl), 2-(7-methyl-2,3-dihydro-benzo[1,4]dioxinyl) and 2-(6-bromo-2,3-dihydro-benzo[1,4]dioxinyl).

In an embodiment of the present invention $R^5$ is selected from the group consisting of halogen and lower alkyl. In another embodiment of the present invention $R^5$ is selected from chloro, fluoro, bromo and methyl.

In an embodiment of the present invention, the stereo-center on the compound of formula (I) is in the S-configuration. In another embodiment of the present invention, the stereo-center on the compound of formula (I) is in the R-configuration.

In an embodiment of the present invention the compound of formula (I) is present as an enantiomerically enriched mixture, wherein the % enantiomeric enrichment (% ee) is greater than about 75%, preferably greater than about 90%, more preferably greater than about 95%, most preferably greater than about 98%.

Additional embodiments of the present invention, include those wherein the substituents selected for one or more of the variables defined herein (i.e. $R^1$, $R^3$, $R^4$, X-Y and A) are independently selected to be any individual substituent or any subset of substituents selected from the complete list as defined herein.

Representative compounds of the present invention, are as listed in Tables 1 below. Additional compounds of the present invention are as listed in Table 3. In Tables 1 and 2 below, the column headed "stereo" defines the stereo-configuration at the carbon atom of the heterocycle attached at the starred bond. Where no designation is listed, the compound was prepared as a mixture of stereo-configurations. Where an "R" or "S" designation is listed, the stereo-configuration was based on the enantiomerically enriched starting material.

TABLE 1

Representative Compounds of Formula (I)

| ID No. | (R) | Stereo | $(CH_2)_a$ | $NR^4$ | $R^1$ | $R^2$ |
|---|---|---|---|---|---|---|
| 1 | 2-(2,3-dihydro-benzo[1,4]dioxinyl) |  | $CH_2$ | NH | H | H |
| 2 | 2-(benzo[1,3]dioxolyl) |  | $CH_2$ | NH | H | H |
| 3 | 3-(3,4-dihydro-2H-benzo[1,4]dioxepinyl) |  | $CH_2$ | NH | H | H |
| 4 | 2-(2,3-dihydro-benzo[1,4]dioxinyl) | S | $CH_2$ | NH | H | H |
| 5 | 2-(2,3-dihydro-benzo[1,4]dioxinyl) | R | $CH_2$ | NH | H | H |
| 6 | 2-(2,3-dihydro-benzo[1,4]dioxinyl) |  | $CH_2$ | NH | methyl | methyl |
| 7 | 2-(2,3-dihydro-benzo[1,4]dioxinyl) |  | $CH_2$ | $N(CH_3)$ | H | H |
| 8 | 2-(6-chloro-2,3-dihydro-benzo[1,4]dioxinyl) | S | $CH_2$ | NH | H | H |
| 9 | 2-(6-fluoro-2,3-dihydro-benzo[1,4]dioxinyl) | S | $CH_2$ | NH | H | H |
| 10 | 2-(chromanyl) |  | $CH_2$ | NH | H | H |
| 13 | 2-(5-fluoro-2,3-dihydro-benzo[1,4]dioxinyl) | S | $CH_2$ | NH | H | H |
| 14 | 2-(7-chloro-2,3-dihydro-benzo[1,4]dioxinyl) | S | $CH_2$ | NH | H | H |
| 15 | 2-(6-chloro-benzo[1,3]dioxolyl) |  | $CH_2$ | NH | H | H |
| 16 | 2-(2,3-dihydro-benzo[1,4]dioxinyl) |  | $CH_2CH_2$ | NH | H | H |
| 18 | 2-(7-nitro-2,3-dihydro-benzo[1,4]dioxinyl) | S | $CH_2$ | NH | H | H |
| 19 | 2-(7-methyl-2,3-dihydro-benzo[1,4]dioxinyl) | S | $CH_2$ | NH | H | H |
| 20 | 2-(5-chloro-2,3-dihydro-benzo[1,4]dioxinyl) | S | $CH_2$ | NH | H | H |
| 22 | 2-(8-methoxy-2,3-dihydro-benzo[1,4]dioxinyl) | S | $CH_2$ | NH | H | H |
| 24 | 2-(6-bromo-2,3-dihydro-benzo[1,4]dioxinyl) | S | $CH_2$ | NH | H | H |
| 29 | 2-(6,7-dichloro-2,3-dihydro-benzo[1,4]dioxinyl) | S | $CH_2$ | NH | H | H |
| 30 | 2-(8-chloro-2,3-dihydro-benzo[1,4]dioxinyl) | S | $CH_2$ | NH | H | H |
| 33 | 2-(2,3-dihydro-naphtho[2,3-b][1,4]dioxinyl) | S | $CH_2$ | NH | H | H |
| 35 | 2-(4-methyl-benzo[1,3]dioxolyl) |  | $CH_2$ | NH | H | H |

TABLE 2

Additional Compounds of the Present Invention

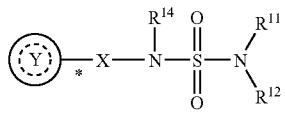

| ID No. | (Y) | Stereo | X | NR$^{14}$ | R$^{11}$ | R$^{12}$ |
|---|---|---|---|---|---|---|
| 23 | 2-(5-methoxy-2,3-dihydro-benzo[1,4]dioxinyl) | S | CH$_2$ | NH | H | H |
| 26 | 2-(6-methylcarbonyl-2,3-dihydro-benzo[1,4]dioxinyl) | S | CH$_2$ | NH | H | H |
| 32 | 2-(6-methoxycarbonyl-2,3-dihydro-benzo[1,4]dioxinyl) | S | CH$_2$ | NH | H | H |
| 34 | 2-(6-hydroxymethyl-2,3-dihydro-benzo[1,4]dioxinyl) | S | CH$_2$ | NH | H | H |
| 36 | 2-(7-amino-2,3-dihydro-benzo[1,4]dioxinyl) | S | CH$_2$ | NH | H | H |

As used herein, unless otherwise noted, "halogen" shall mean chlorine, bromine, fluorine and iodine.

As used herein, unless otherwise noted, the term "alkyl" whether used alone or as part of a substituent group, includes straight and branched chains. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1-4 carbon atoms.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, the notation "*" shall denote the presence of a stereogenic center.

When a particular group is "substituted" (e.g., alkyl, aryl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

Under standard nomenclature used throughout this disclosure, the terminal portion of the designated side chain is described first, followed by the adjacent functionality toward the point of attachment. Thus, for example, a "phenyl-alkyl-amino-carbonyl-alkyl" substituent refers to a group of the formula

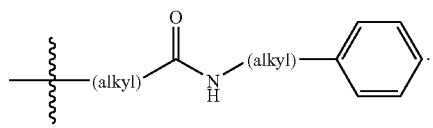

Abbreviations used in the specification, particularly the Schemes and Examples, are as follows:

| | |
|---|---|
| DCC = | Dicyclohexyl Carbodiimide |
| DCE = | Dichloroethane |
| DCM = | Dichloromethane |
| DIPEA or DIEA = | Diisopropylethylamine |
| DMF = | N,N-Dimethylformamide |
| DMSO = | Dimethylsulfoxide |
| EDC = | Ethylcarbodiimide |
| Et$_3$N or TEA = | Triethylamine |
| Et$_2$O = | Diethyl ether |
| EA or EtOAc = | Ethyl acetate |
| EtOH = | Ethanol |
| IPA = | 2-propanol |
| Hept = | Heptane |
| HOBT = | 1-Hydroxybenzotriazole |
| HPLC = | High Pressure Liquid Chromatography |
| LAH = | Lithium Aluminum Hydride |
| M or MeOH = | Methanol |
| NMR = | Nuclear Magnetic Resonance |
| Pd—C = | Palladium on Carbon Catalyst |
| RP HPLC = | Reverse Phase High Pressure Liquid Chromatography |
| RT or rt = | Room temperature |
| TEA = | Triethylamine |
| TFA = | Trifluoroacetic Acid |
| THF = | Tetrahydrofuran |
| TLC = | Thin Layer Chromatography |

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:

acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydrocy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1 H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Compounds of formula (I) may be prepared according to the process outlined in Scheme 1.

Accordingly, a suitably substituted compound of formula (X), a known compound or compound prepared by known methods, is reacted with sulfamide, a known compound, preferably wherein the sulfamide is present in an amount in the range of about 2 to about 5 equivalents, in an organic solvent such as THF, dioxane, and the like, preferably at an elevated temperature in the range of about 50° C. to about 100° C., more preferably at about reflux temperature, to yield the corresponding compound of formula (Ia).

Alternatively, a suitably substituted compound of formula (X), a known compound or compound prepared by known methods, is reacted with a suitably substituted compound of formula (XI), a known compound or compound prepared by known methods, in the presence of a base such as TEA, DIPEA, pyridine, and the like, in an organic solvent such as DMF, DMSO, and the like, to yield the corresponding compound of formula (I).

Compounds of formula (X) wherein

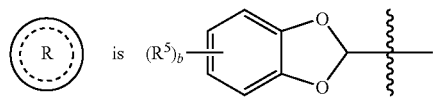

may be prepared according to the process outlined in Scheme 2.

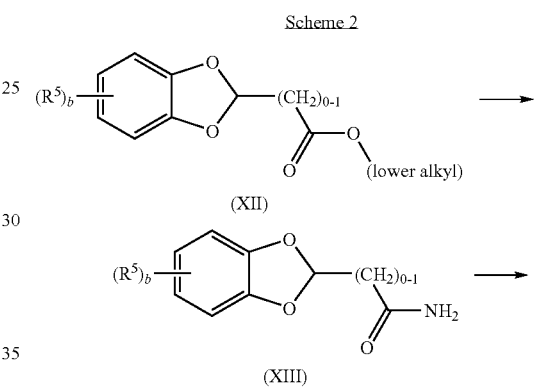

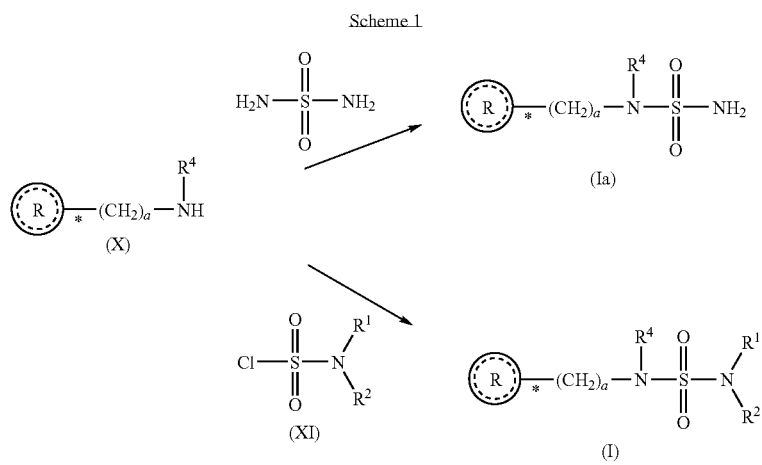

-continued

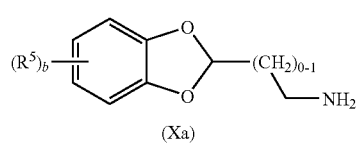

Accordingly, a suitably substituted compound of formula (XII), a known compound or compound prepared by known method (for example as described in Scheme 3 above) is reacted with NH$_4$OH, a known compound, optionally in an organic solvent such as acetonitrile, and the like, to yield the corresponding compound of formula (XIII).

The compound of formula (XIII) is reacted with a suitably selected reducing agent, such as LAH, and the like, in an organic solvent such as THF, diethyl ether, and the like, to yield the corresponding compound of formula (Xa).

Compounds of formula (X) wherein

is selected from

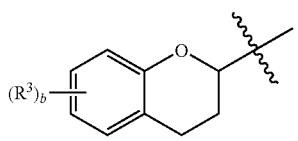

may be prepared according to the process outlined in Scheme 3.

Scheme 3

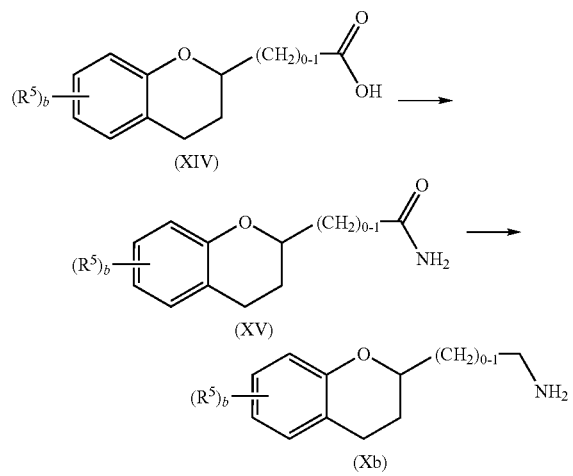

Accordingly, a suitably substituted compound of formula (XIV), a known compound or compound prepared by known methods, is reacted with NH$_4$OH, in the presence of a coupling agent such as DCC, and the like, optionally in an organic solvent such as acetonitrile, and the like, to yield the corresponding compound of formula (XV).

The compound of formula (XV) is reacted with a suitably selected reducing agent, such as LAH, and the like, in an organic solvent such as THF, diethyl ether, and the like, to yield the corresponding compound of formula (Xb).

Compounds of formula (X) wherein

is selected from

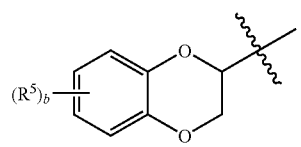

and wherein a is 2, may be prepared according to the process outlined in Scheme 4.

Scheme 5

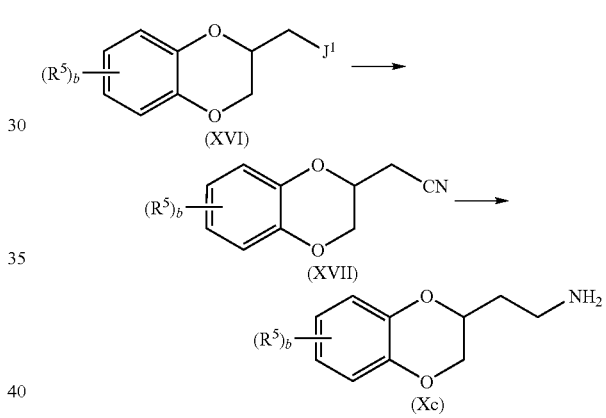

Accordingly, a suitably substituted compound of formula (XVI) wherein J$^1$ is a suitable leaving group such as Br, Cl, I, tosyl, mesyl, triflyl, and the like, a known compound or compound prepared by known methods (for example, by activating the corresponding compound wherein J$^1$ is OH), is reacted with a cyanide such as potassium cyanide, sodium cyanide, and the like, in an organic solvent such as DMSO, DMF, THF, and the like, to yield the corresponding compound of formula (XVII).

The compound of formula (XVII) is reduced according to known methods, for example by reacting with a suitable reducing agent such as LAH, borane, and the like, to yield the corresponding compound of formula (Xc).

Compounds of formula (X) wherein

is selected from

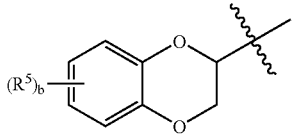

and wherein a is 1, may be prepared according to the process outlined in Scheme 5.

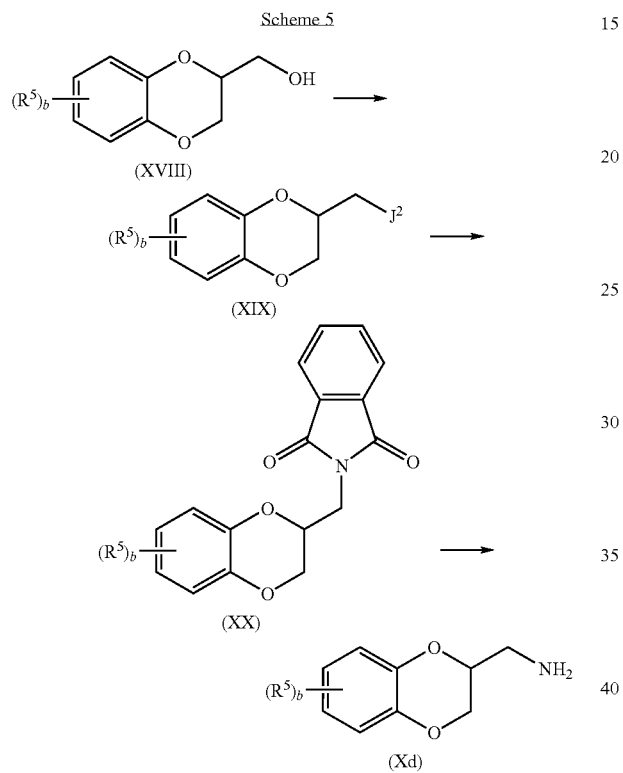

Accordingly, a suitably substituted compound of formula (XVIII), a known compound or compound prepared by known methods is activated, according to known method, to yield the corresponding compound of formula (XIX), wherein $J^2$ is a suitable leaving group, such tosylate, Cl, Br, I, mesylate, triflate, and the like.

The compound of formula (XIX) is reacted with a phthalimide salt such as potassium phthlimide, sodium phthalimide, and the like, in an organic solvent such as DMF, DMSO, acetonitrile, and the like, preferably, at an elevated temperature in the range of from 50° C. to about 200° C., more preferably, at about reflux temperature, to yield the corresponding compound of formula (XX).

The compound of formula (XX) is reacted with $N_2H_4$, a known compound, in an organic solvent such as ethanol, methanol, and the like, preferably, at an elevated temperature in the range of from about 50° C. to about 100° C., more preferably, at about reflux temperature, and the like, to yield the corresponding compound of formula (Xd).

One skilled in the art will recognize that compounds of formula (X) wherein

is selected from

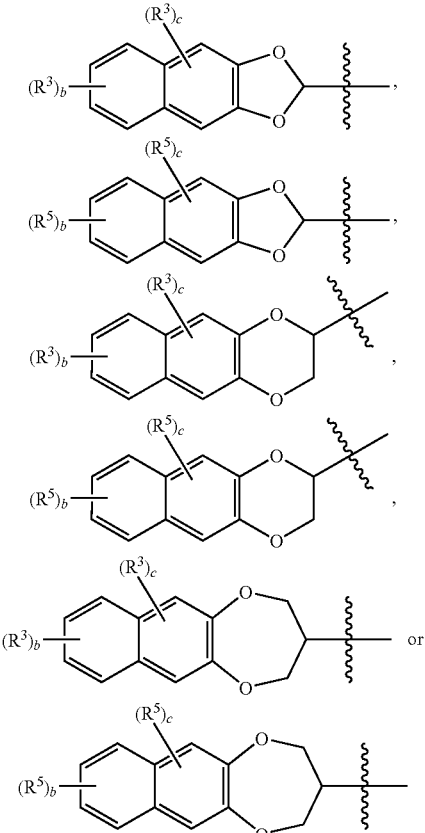

may be similarly prepared according to known methods or for example, according to the processes outlined in Schemes 2 through 5 above, by selecting and substituting the corresponding naphthyl-fused compounds for the benzo-fused starting materials.

One skilled in the art will further recognize that wherein a single enantiomer (or a mixture of enantiomers wherein one enantiomer is enriched) of a compound of formula (X) is desired, the above processes as described in Schemes 1 through 5 may be applied by substituting the corresponding single enantiomer (or mixture of enantiomers wherein one enantiomer is enriched) for the appropriate starting material.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.1-1000 mg and may be given at a dosage of from about 0.01-200.0 mg/kg/day, preferably from about 0.1 to 100 mg/kg/day, more preferably from about 0.5-50 mg/kg/day, more preferably from about 1.0-25.0 mg/kg/day, more preferably from about 0.5-10.0 mg/kg/day, most preferably from about 1.0 to about 5.0 mg/kg/day, or any range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 1000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating depression described in the present invention may also be carried out using a pharmaceutical composition comprising any of the compounds as defined herein and a pharmaceutically acceptable carrier. The pharmaceutical composition may contain between about 0.1 mg and 1000 mg, preferably about 50 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

Compounds of this invention may be administered in any of the foregoing compositions and according to dosage regimens established in the art whenever treatment of depression is required.

The daily dosage of the products may be varied over a wide range from 0.01 to 200 mg/kg per adult human per day or any range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250, 500 and 1000 milligrams of the active ingredient for the symptomatic adjustment of the dosage to the patient to be treated. An effective amount of the drug is ordinarily supplied at a dosage level of from about 0.01 mg/kg to about 200 mg/kg of body weight per day. Preferably, the range is from about 0.1 to about 100.0 mg/kg of body weight per day, more preferably, from about 0.5 mg/kg to about 50 mg/kg, more preferably, from about 1.0 to about 25.0 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

EXAMPLE 1

((3,4-Dihydro-2H-benzo[b][1,4]dioxepin-3-yl)methyl)sulfamide (Compound #3)

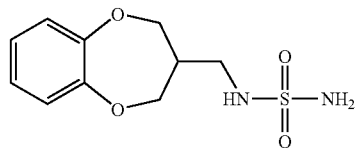 [SMILES: NS(=O)(=O)NCC1COc2ccccc2OC1]

Catechol (5.09 g, 46.2 mmol) and potassium carbonate were combined in acetonitrile and heated to reflux for one hour. 2-Chloromethyl-3-chloro-1-propene (5.78 g, 46.2 mmol) was added and the reaction was continued at reflux for 24 hours. The solution was cooled to room temperature and filtered. The filtrate was evaporated and the residue was diluted with water and extracted with diethyl ether (3×). The combined organic solution was dried over $MgSO_4$ and concentrated. Chromatography (2% ethyl ether in hexane) yielded 3-methylene-3,4-dihydro-2H-benzo[b][1,4]dioxepine as a colorless oil.

MS (ESI): 163.2 (M+H$^+$) $^1$H NMR (300 MHz, CDCl$_3$), δ: 6.94 (m, 4H), 5.07 (s, 2H), 4.76 (s, 4H).

3-Methylene-3,4-dihydro-2H-benzo[b][1,4]dioxepine (5.00 g, 30.8 mmol) was dissolved in dry THF (100 mL). Borane-THF (1.0 M in THF, 10.3 mL) was added at 0° C. The reaction was stirred at RT for 5 hours. Aminosulfonic acid (6.97 g, 61.6 mmol) was added. The reaction was heated to reflux overnight. The reaction was cooled to room temperature and aqueous sodium hydroxide (3.0 M, 100 mL) was added. The solution was extracted with ethyl acetate (3×100 mL). The combined organic solution was dried over $MgSO_4$. The solution was concentrated under vacuum and purified by chromatography (2% to 8% methanol in dichloromethane) to yield ((3,4-dihydro-2H-benzo[b][1,4]dioxepin-3-yl)methyl) amine as a colorless oil.

MS (ESI): 180.1 (M+H+) ¹H NMR (300 MHz, DMSO), δ: 6.92 (m, 4H), 4.21 (m, 2H), 4.07 (m, 2H), 3.33 (broad, 2H), 3.16 (d, J=4 Hz, 1H), 2.72 (d, J=4 Hz, 1H), 2.30 (m, 1H).

((3,4-Dihydro-2H-benzo[b][1,4]dioxepin-3-yl)methyl) amine (2.90 g, 16.2 mmol) and sulfamide (3.11 g, 32.4 mmol) were combined in dry dioxane (60 ml) and heated to reflux overnight. Chloroform was added and the precipitate was removed by filtration. The filtrate was concentrated under vacuum and purified by chromatography (2% to 8% acetone in dichloromethane) to yield the title compound as an off-white solid.

258.8 (M+H+) ¹H NMR (300 MHz, DMSO), δ: 6.92 (m, 4H), 6.71 (broad, 1H), 6.59 (broad, 2H), 4.19 (m, 2H), 4.04 (m, 2H), 3.00 (m, 2H), 2.39 (m, 1H).

EXAMPLE 2

N-(2,3-Dihydro-benzo[4]dioxin-2-ylmethyl)-sulfamide (Compound #1)

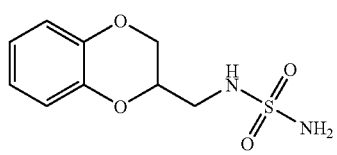 [SMILES: NS(=O)(=O)NCC1COc2ccccc2O1]

Racemic 2,3-dihydro-1,4-benzdioxin-2-ylmethylamine (4.4 g, 26 mmol) and sulfamide (5.1 g, 53 mmol) were combined in 1,4 dioxane (100 mL) and refluxed for 2 h. The reaction was cooled to room temperature and a small amount of solid was filtered and discarded. The filtrate was evaporated in vacuo and the residue was purified using flash column chromatography (DCM:Methanol—10:1) to yield a white solid. The solid was recrystallized from DCM to yield the title compound as a white solid.

mp: 97.5-98.5° C. Elemental Analysis: Anal Calc: C, 44.25; H, 4.95; N, 11.47; S, 13.13. Anal Found: C, 44.28; H, 4.66; N, 11.21; S, 13.15. H¹NMR (DMSO d6) δ 6.85 (m, 4H), 6.68 (bd s, 3H, NH), 4.28 (m, 2H), 3.97 (dd, J=6.9,11.4 Hz, 1H), 3.20 (m, 1H), 3.10 (m, 1H).

EXAMPLE 3

(Benzo[1,3]dioxol-2-ylmethyl)sulfamide (Compound #2)

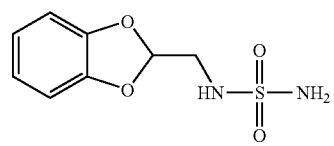 [SMILES: NS(=O)(=O)NCC1Oc2ccccc2O1]

Catechol (10.26 g, 93.2 mmol), sodium methoxide (25% by weight in methanol, 40.3 g, 186 mmol), and methyl dichloroacetate (13.3 g, 93.2 mmol) were combined in dry methanol (100 mL). The solution was heated to reflux overnight. The reaction was cooled to room temperature, acidified by addition of concentrated hydrochloric acid and then reduced in volume under vacuum to about 50 mL. Water was added and the mixture was extracted with diethyl ether (3×100 mL). The combined organic solution was dried with MgSO₄, concentrated to a brown solid, and chromatographed (2% ethyl acetate in hexane) to yield benzo[1,3]dioxole-2-carboxylic acid methyl ester as a colorless oil.

MS (ESI): 195.10 (M+H+). ¹H NMR (300 MHz, CDCl₃), δ: 6.89 (broad, 4H), 6.29 (s, 1H), 4.34 (q, J=7 Hz, 2H), 1.33 (t, J=7 Hz, 3H).

To benzo[1,3]dioxole-2-carboxylic acid methyl ester (7.21 g, 40.0 mmol) was added ammonium hydroxide (29% in water, 10 mL) and enough acetonitrile to make the mixture homogeneous (~5 mL). The solution was stirred for two hours at room temperature and then distilled water was added. Benzo[1,3]dioxole-2-carboxylic acid amide precipitated as a white solid and was collected by filtration and used without further purification.

MS (ESI): 160.00 (M+H+) ¹H NMR (300 MHz, DMSO), δ: 7.99 (s, broad, 1H), 7.72 (s, broad, 1H), 6.94 (m, 2H) 6.86 (m, 2H), 6.30 (s, 1H).

Benzo[1,3]dioxole-2-carboxylic acid amide (5.44 g, 32.9 mmol) was dissolved in tetrahydrofuran (THF, 100 mL). Lithium aluminum hydride (LAH, 1M in THF, 39.5 mL, 39.5 mmol) was added slowly to the solution at room temperature. The reaction was stirred at room temperature for 24 hours. Distilled water was added to destroy the excess LAH. Aqueous sodium hydroxide (3.0 M, 100 mL) was added and the solution was extracted with ethyl acetate (3×100 mL). The combined organic solution was washed with water and dried over MgSO₄. The solvent was evaporated to yield C-benzo[1,3]dioxol-2-yl-methylamine as a colorless oil.

MS (ESI): 152.1 (M+H+) ¹H NMR (300 MHz, CDCl₃), δ: 6.87 (m, 4H), 6.09 (t, J=4 Hz, 1H), 3.13 (d, J=4 Hz, 2H)

C-Benzo[1,3]dioxol-2-yl-methylamine (2.94 g, 19.4 mmol) and sulfamide (3.74 g, 38.9 mmol) were combined in dry dioxane (50 mL) and the solution was heated to reflux overnight. The reaction was concentrated and the residue was chromatographed (2% to 10% acetone in dichloromethane) to yield the title compound as a white solid.

MS (ESI): 230.0 (M+H+) ¹H NMR (300 MHz, CDCl₃), δ: 6.87 (m, 4H), 6.25 (t, J=4 Hz, 1H), 4.79 (broad, 1H), 4.62 (broad, 1H), 3.64 (d, J=4 Hz, 2H).

EXAMPLE 4

(2S)-(−)-N-(2,3-Dihydro-benzo[1,4]dioxin-2-ylmethyl)-sulfamide (Compound #4)

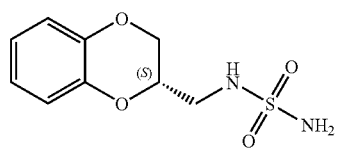

Catechol (13.2 g, 0.12 mol) and potassium carbonate (16.6 g, 0.12 mol) were stirred in DMF (250 mL) and (2R)-glycidyl tosylate (22.8 g, 0.10 mol) was added and the reaction was stirred at 60° C. for 24 h. The reaction was cooled to room temperature and diluted with ice water (1 L) and extracted with diethyl ether (4 times). The combined organic solution was washed 3 times with 10% potassium carbonate, once with water, once with brine and evaporated in vacuo to yield a white solid which was purified by flash column chromatography (DCM:Methanol—50:1) to yield ((2S)-2,3-dihydro-benzo[1,4]dioxin-2-yl)-methanol as a solid.

The solid (13.3 g, 68 mmol) was dissolved in pyridine (85 mL) cooled to 0° C., p-toluenesulfonyl chloride (13.0 g, 68 mmol) was added and the reaction mixture stirred at room temperature for 20 h. The reaction was diluted with diethyl ether (1 L) and 1N HCl (1.2 L). The organic layer was separated and washed 2 times with 1N HCl (500 mL), 4 times with water (150 mL), once with brine, dried (MgSO$_4$) and evaporated in vacuo to yield a white solid which was purified by flash column chromatography (Hept:EA—2:1) to yield toluene-4-sulfonic acid (2S)-2,3-dihydro-benzo[1,4]dioxin-2-ylmethyl ester as a white solid.

The white solid was combined with potassium phthalimide (14.4 g, 78 mmol) in DMF (250 mL) and heated to reflux for 1 h, cooled to room temperature and poured into vigorously stirring water (1.5 L) and stirred 30 min. White solid was filtered and the solid was washed several times with water, 2% NaOH, and water again and let air dry to yield a (2S)-2-(2,3-Dihydro-benzo[1,4]dioxin-2-ylmethyl)-isoindole-1,3-dione as white powdery solid.

The powdery white solid was combined with hydrazine (2.75 g, 86 mmol) in EtOH (225 mL) and heated at reflux for 2 h, cooled to room temperature and 1 N HCl added to pH 1.0 and stirred for 15 min. White solid was filtered and washed with fresh EtOH (solid discarded) and the filtrate was evaporated in vacuo to a solid, which was partitioned between diethyl ether and dilute aqueous NaOH. The diethyl ether solution was dried (Na$_2$SO$_4$) and evaporated in vacuo to a yield a light yellow oil. The oil was purified by flash column chromatography (DCM:MeOH—10:1) to yield an oil. A portion of the oil (4.82 g, 29 mmol) in 2-propanol (250 mL) was treated with 1N HCl (30 mL) and heated on steambath until homogeneous and then let cool to room temperature. After 3 h, the mixture was ice cooled for 2 h. A white flaky solid (the corresponding HCl salt of (2S)-C-(2,3-Dihydro-benzo[1,4]dioxin-2-yl)-methylamine) was filtered off and then recrystallized again from 2-propanol to yield a white solid.

$[\alpha]_D = -69.6$ (c=1.06, EtOH)

The white solid was partitioned between DCM and dilute NaOH, and the DCM was dried (NaSO$_4$) and evaporated in vacuo to yield (2S)-C-(2,3-Dihydro-benzo[1,4]dioxin-2-yl)-methylamine as an oil.

$[\alpha]_D = -57.8$ (c=1.40, CHCl$_3$)

The oil (2.1 g, 12.7 mmol) and sulfamide (2.44 g, 25.4 mmol) were refluxed in dioxane (75 mL) for 2 h and the crude product was purified by flash column chromatography (DCM:MeOH 10:1) to yield a white solid, which was recrystallized from DCM to yield the title compound as a white crystalline solid.

mp 102-103° C. $[\alpha]_D = -45.1°$ (c=1.05, M); $^1$H NMR (DMSOd6) δ 6.86 (m, 4H), 6.81 (bd s, 3H, NH), 4.3 (m, 2H), 3.97 (dd, J=6.9, 11.4 Hz, 1H), 3.20 (dd, J=5.5, 13.7 Hz, 1H), 3.10 (dd, J=6.9, 13.7 Hz, 1H) Elemental Analysis: Anal Calc: C, 44.25; H, 4.95; N, 11.47; S, 13.13. Anal Found: C, 44.20; H, 4.69; N, 11.40; S, 13.22.

EXAMPLE 5

N-(2,3-Dihydro-benzo[1,4]dioxin-2-ylmethyl)-N',N' dimethylsulfamide (Compound #6)

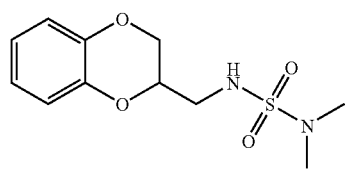 [SMILES: CN(C)S(=O)(=O)NCC1COc2ccccc2O1]

Racemic 2,3-dihydro-1,4-benzdioxin-2-ylmethylamine (8.25 g, 5.0 mmol) and triethylamine (1.52 g, 15 mmol) were combined in DMF (10 mL) and cooled in an ice bath as dimethylsulfamoyl chloride (1.44 g, 10 mmol) was added. The reaction mixture was then stirred for 3 hr with continued cooling. The reaction mixture was partitioned between ethyl acetate and water, and the ethyl acetate solution was washed with brine, dried (MgSO$_4$) and evaporated in vacuo to yield an oil. The oil was purified using flash column chromatography (ethyl acetate:Heptane—1:1) to yield a white solid, which was recrystallized (ethyl acetate/Hexane) to yield the title compound as a white floccular solid.

mp 76-78° C. MS 273 (MH$^+$) Elemental Analysis: Anal Calc: C, 48.52; H, 5.92; N, 10.29; S, 11.78. Anal Found: C, 48.63; H, 5.62; N, 10.20; S, 11.90. $^1$H NMR (CDCl$_3$) δ 6.87 (m, 4H), 4.59 (bd m, 1H, NH), 4.35 (m, 1H), 4.27 (dd, J=2.3, 11.4 Hz, 1H), 4.04 (dd, J=7.0, 11.4, 1H), 3.36 (m, 2H), 2.82 (s, 6H).

EXAMPLE 6

N-(2,3-Dihydro-benzo[4,1]dioxin-2-ylmethyl)-N-methylsulfamide (Compound #7)

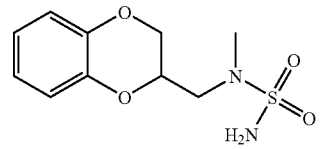 [SMILES: CN(CC1COc2ccccc2O1)S(N)(=O)=O]

Racemic 2,3-dihydro-1,4-benzdioxin-2-ylmethylamine (825 mg, 5 mmol) was dissolved in ethyl formate (15 mL), refluxed for 30 min and evaporated in vacuo to yield N-(2,3-dihydro-benzo[1,4]dioxin-2-ylmethyl)-formamide as an oil.

The oil in diethyl ether (25 mL) was treated with 1M LAH in THF (9.0 mL, 9.0 mmol) at 0° C. and stirred for 5 h at room temperature. The reaction was cooled in an ice bath and quenched with water (0.50 mL), followed by 3 N NaOH (0.50 mL) and water (0.50 mL). The mixture was then stirred at room temperature for 1 h. Solid was filtered and the filtrate was evaporated in vacuo to yield a residue which was partitioned between 1N HCl and diethyl ether. The aqueous phase was basified with 1N NaOH and extracted with diethyl ether. The organic phase was dried (MgSO$_4$) and evaporated in vacuo to yield (2,3-dihydro-benzo[1,4]dioxin-2-ylmethyl)-methyl-amine as an oil.

MS 180 (MH$^+$) $^1$H NMR (CDCl$_3$) δ 6.85 (m, 4H), 4.30 (m, 2H), 4.02 (dd, J=7.9, 11.6 Hz, 1H), 2.85 (m, 2H), 2.50 (s, 3H)

The oil (380 mg, 2.1 mmol) and sulfamide (820 mg, 8.5 mmol) were combined in dioxane (15 mL), refluxed for 1.5 h and evaporated in vacuo to yield a crude residue. The residue was purified via column chromatography (ethyl acetate/Heptane 1:1) and the resultant solid was recrystallized from ethyl acetate/Hexane to yield the title compound as a white solid.

mp 97-98° C. MS 257 (M⁻¹) Elemental Analysis: Anal Calc: C, 46.50; H, 5.46; N, 10.85; S, 12.41. Anal Found: C, 46.48; H, 5.65; N, 10.90; S, 12.07. ¹H NMR (CDCl₃) δ 6.86 (m, 4H), 4.52 (bs, 2H), 4.46 (m, 1H), 4.29 (dd, J=2.3, 11.5 Hz, 1H), 4.05 (dd, J=6.5, 11.5 Hz, 1H), 3.51 (dd, J=6.7, 14.9 Hz, 1H), 3.40 (dd, J=5.9, 14.9 Hz, 1H), 2.99 (s, 3H).

EXAMPLE 7

(2S)-(−)-N-(6-Chloro-2,3-dihydro-benzo[1,4]dioxin-2-ylmethyl)-sulfamide (Compound #8)

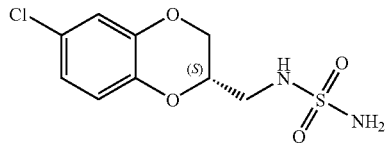

Following the procedure outlined in Example 4 above, 4-chlorocatechol was reacted to yield a mixture of (2S)-C-(7-Chloro-2,3-dihydro-benzo[1,4]dioxin-2-yl)-methylamine and (2S)-C-(6-Chloro-2,3-dihydro-benzo[1,4]dioxin-2-yl)-methylamine (ca. 3:1 ratio of 6-chloro:7-chloro isomers by RP HPLC).

The mixture was dissolved in 2-propanol (100 mL) and 1N HCl in diethyl ether was added until pH=1.0 was attained. The hydrochloride salt that precipitated was filtered (2.65 g) and re-crystallized from methanol/IPA to yield white crystals. The white crystals were partitioned between DCM and dilute NaOH. The DCM was dried and evaporated in vacuo to yield purified (2S)-C-(6-Chloro-2,3-dihydro-benzo[1,4]dioxin-2-yl)-methylamine as an oil.

[α]_D=−67.8 (c=1.51, CHCl₃)

The oil (7.75 mmol) and sulfamide (1.50 g, 15.5 mmol) were combined in dioxane (50 mL) and refluxed for 2.0 h, cooled to room temperature and evaporated in vacuo to yield a solid. The product was purified via flash column chromatography using DCM/methanol 20:1 to yield the title compound as a white solid.

MS 277 (M⁻¹) [α]_D=−59.9° (c=1.11, M) ¹H NMR (CDCl₃) δ 6.90 (d, J=2.2 Hz, 1H), 6.81 (m, 2H), 4.76 (m, 1H), 4.55 (s, 2H), 4.40 (m, 1H), 4.29 (dd, J=2.4, 11.5 Hz, 1H), 4.05 (dd, J=7.1, 11.5 Hz, 1H), 3.45 (m, 2H) Elemental Analysis: Anal Calc: C, 38.78; H, 3.98; N, 10.05. Anal Found: C, 38.80; H, 3.67; N, 9.99.

The filtrates of the crystallized hydrochloride salt of (2S)-C-(6-Chloro-2,3-dihydro-benzo[1,4]dioxin-2-yl)-methylamine prepared above were recovered (ca. 1:1 of 6-chloro:7-chloro isomers) and evaporated in vacuo to yield a solid, which was partitioned between DCM (200 mL) and dilute NaOH (0.5 M, 50 mL). The DCM solution was washed once with brine, dried (Na₂SO₄) and evaporated in vacuo to yield an oil, which was purified via reverse phase HPLC (10-50% ACN with 0.16% TFA in water with 0.20% TFA) to yield (2S)-C-(7-Chloro-2,3-dihydro-benzo[1,4]dioxin-2-yl)-methylamine as a residue.

The residue was combined with sulfamide (0.90 g, 9.4 mmol) in dioxane (25 mL) and refluxed for 2.5 h, cooled to room temperature and evaporated in vacuo to yield an oil. The oil was purified by flash column chromatography using DCM/methanol—10:1 to yield (2S)-(−)-N-(7-Chloro-2,3-dihydro-benzo[1,4]dioxin-2-ylmethyl)-sulfamide as a white solid.

MS 277 (M⁻¹) ¹H NMR (CDCl₃/CD₃OD) δ 6.88 (d, J=0.7 Hz, 1H), 6.81 (m, 2H), 4.37 (m, 1H), 4.30 (dd, J=2.3, 11.6 Hz, 1H), 4.04 (dd, J=7.0, 11.6 Hz, 1H), 3.38 (m, 2H).

EXAMPLE 8

Chroman-2-ylmethylsulfamide (Compound #10)

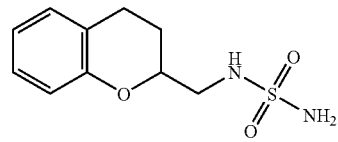 [SMILES: NS(=O)(=O)NCC1CCc2ccccc2O1]

Chroman-2-carboxylic acid (4.5 g, 25 mmol) and HOBT (3.86 g, 25 mmol) were combined in DCM (40 mL) and DMF (10 mL). Dimethylaminopropyl ethylcarbodiimide (EDC, 4.84 g, 25 mmol) was added at room temperature and the reaction mixture was stirred for 30 min. Ammonium hydroxide (2.26 mL, 33.4 mmol) was added and the reaction mixture was stirred for 16h. The reaction mixture was diluted with DCM (50 mL) and water (50 mL) and the pH of the mixture was adjusted to about pH=3.0 with 1 N HCl. The DCM was separated and the aqueous phase extracted twice with DCM. The combined DCM phase was dried (Na₂SO₄) and evaporated in vacuo to yield an oil, which was purified with flash column chromatography (ethyl acetate) to yield an oil.

The oil (5.35 g, 30 mmol) in THF (90 mL) was stirred as 1 M LAH in THF (36 mL, 36 mmol) was added and the reaction mixture was then stirred at room temperature for 20 h. The reaction was quenched with water, stirred for 2 hours, the solution decanted, dried (Na₂SO₄) and evaporated in vacuo to yield C-chroman-2-yl-methylamine as an oily amine.

The oily amine (1.63 g, 10 mmol) and sulfamide (1.92 g, 20 mmol) were combined in dioxane (50 mL) and brought to reflux for 2 h. The solution was cooled and evaporated in vacuo to yield an oil, which was purified via column chromatography (DCM:Methanol 10:1) to yield a white solid. The solid was recrystallized from ethyl acetate/hexane to yield chroman-2-ylmethylsulfamide as a white solid.

mp 100-101° C. MS 241 (M⁻¹) Elemental Analysis: Anal Calc: C, 49.57; H, 5.82; N, 11.56; S, 13.23. Anal Found: C, 49.57; H, 5.80; N, 11.75; S, 13.33.

EXAMPLE 9

2-(2,3-Dihydro-benzo[1,4]dioxin-2-yl)-ethylsulfamide (Compound #16)

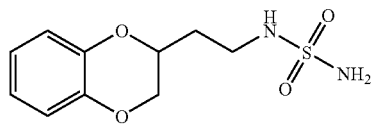 [SMILES: NS(=O)(=O)NCCC1COc2ccccc2O1]

Potassium cyanide (2.05 g, 31.5 mmol) was added to 2-bromomethyl-(2,3 dihydrobenzo[1,4]dioxine) (6.87 g, 30 mmol) in DMSO (90 mL) and stirred at ambient temperature for 20 h. The reaction mixture was then diluted with water (250 mL) and extracted twice with diethyl ether. The diethyl ether was washed with water, then washed twice with brine, dried ($Na_2SO_4$) and evaporated in vacuo to yield 2-cyanomethyl-(2,3 dihydrobenzo[1,4]dioxine) as a white solid.

$^1$H NMR ($CDCl_3$) δ 6.89 (m, 4H), 4.50 (m, 1H), 4.31 (dd, J=2.3, 11.5 Hz, 1H), 4.08 (dd, J=6.2,11.6 Hz, 1H), 2.78 (d, J=6.1, Hz, 2H)

The 2-cyanomethyl-(2,3 dihydrobenzo[1,4]dioxine) was dissolved in THF (50 mL) and 1M $BH_3$ in THF (80 mL, 80 mmol) was added and the reaction mixture refluxed for 5 h, then stirred at ambient temperature for 16 h. With ice bath cooling, 2N HCl was added until pH=1.0 was achieved. The reaction mixture was then stirred for 1 h at room temperature and evaporated in vacuo to yield an oil. The oil was partitioned between 3N NaOH and diethyl ether, and the diethyl ether solution was washed with brine, dried ($Na_2SO_4$) and evaporated in vacuo to yield crude 2-(2,3 dihydrobenzo[1,4]dioxin-2-yl)ethylamine.

MS (M+H)$^+$ 180.

The crude 2-(2,3 dihydrobenzo[1,4]dioxin-2-yl)ethylamine in dioxane (100 mL) was combined with sulfamide (3.0 g, 31 mmol) and heated to reflux for 2 h. The solution was cooled and evaporated in vacuo to yield an orange solid, which was purified by column chromatography (DCM:MeOH—10:1) to yield a white solid. The solid was re-crystallized from DCM to yield the title compound as a solid.

MS (M−1) 257 MP 101-103° C. (corr) $^1$H NMR ($CDCl_3$): δ 6.86 (m, 4H), 4.70 (m, 1H), 4.52 (s, 2H), 4.30 (m, 2H), 3.94 (dd, J=7.4, 11.3 Hz, 1H), 3.43 (dd, J=6.4, 12.9 Hz, 2H), 1.94 (dd, J=6.5, 12.9, 2H). Elemental Analysis: Measured: C, 46.48; H, 5.60; N, 10.81; S, 12.41 Calculated: C, 46.50; H, 5.46; N, 10.85; S, 12.41.

EXAMPLE 10

(2S)-(−)-N-(6,7 Dichloro-2,3-dihydro-benzo[1,4]dioxin-2-ylmethyl)-sulfamide (Compound #29)

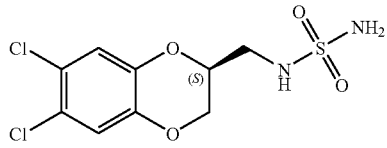

4,5 Dichloroatechol (8.6 g, 48 mmol) and potassium carbonate (6.64 g, 48 mmol) were stirred in DMF (200 mL). (2R)-Glycidyl tosylate (9.12 g, 40 mmol) was added and the reaction mixture was stirred at 60° C. for 24 h. The reaction mixture was cooled to room temperature and then diluted with ice water (600 mL) and extracted with diethyl ether (4 times). The combined organic solution was washed 3 times with 10% potassium carbonate, twice with brine, dried ($MgSO_4$) and evaporated in vacuo to yield a viscous oil of (2S)-2-(6,7-dichloro-2,3-dihydro-benzo[1,4]dioxine)methanol.

The (2S)-2-(6,7 dichloro-2,3-dihydro-benzo[1,4]dioxine)methanol oil (6.4 g, 27 mmol) was dissolved in pyridine (50 mL) cooled to 0° C. Then, p-toluenesulfonyl chloride (5.2 g, 27 mmol) was added and the reaction mixture was stirred at room temperature for 20 h. The reaction mixture was diluted with diethyl ether and 1N HCl (750 mL) and the organic layer was separated and washed 2 times with 1N HCl (250 mL), once with water (150 mL), twice with brine, dried ($MgSO_4$) and evaporated in vacuo to yield light yellow solid of toluene-4-sulfonic acid (2S)-6,7-dichloro-2,3-dihydro-benzo[1,4]dioxin-2-ylmethyl ester.

$^1$H NMR ($CDCl_3$): δ 7.79 (d, J=8.3 Hz, 2H), 7.36 (d, J=8.0 Hz, 2H), 6.94 (s, 1H), 6.83 (s, 1H), 4.37 (m, 1H), 4.2 (m, 3H), 4.03 (dd, J=6.3, 11.7 Hz, 1H), 2.47 (s, 3H).

Toluene-4-sulfonic acid (2S)-6,7-dichloro-2,3-dihydro-benzo[1,4]dioxin-2-ylmethyl ester (8.0 g, 20.5 mmol) was combined with potassium phthalimide (6.1 g, 33 mmol) in DMF (75 mL) and heated to reflux for 1 h, cooled to room temperature and poured into vigorously stirring water (0.5 L) and then stirred 30 min. White solid was filtered and the solid was washed several times with water, 2% NaOH, and water again and then let air dry to yield (2S)-2-(6,7-dichloro-2,3-dihydro-benzo[1,4]dioxin-2-ylmethyl)-isoindole-1,3-dione (6.0 g, 80%) as a white powdery solid.

The white powdery solid was combined with hydrazine (1.06 g, 33 mmol) in EtOH (80 mL) and heated at reflux for 2 h, then cooled to room temperature. 1N HCl was added to adjust the reaction mixture's pH to pH 1.0 and the reaction mixture was then stirred for 15 min. White solid was filtered and washed with fresh EtOH (solid discarded) and the filtrate was evaporated in vacuo to a solid, which was partitioned between diethyl ether and dilute aqueous NaOH. The diethyl ether solution was dried ($Na_2SO_4$) and evaporated in vacuo to a yield a viscous oil of (2S)-2-aminomethyl-(6,7-dichloro-2,3-dihydro-benzo[1,4]dioxine).

$^1$H NMR (CDCl3): δ 6.98 (s, 1H), 6.96 (s, 1H), 4.25 (dd, J=2.0, 11.2 Hz, 1H), 4.15 (m, 1H), 4.0 (m, 1H), 2.97 (d, J=5.5 Hz, 2H)

A portion of the oil (3.8 g, 16 mmol) and sulfamide (3.1 g, 32.4 mmol) were refluxed in dioxane (100 mL) for 2 h and the crude product was purified by flash column chromatography (DCM:MeOH 20:1) to yield the title compound as a white solid, which was recrystallized from ethyl acetate/hexane to yield the title compound as a white crystalline solid.

MS [M−H]$^−$ 31 1.0 mp 119-121° C. [α]$_D$=−53.4° (c=1.17, M) $^1$H NMR (DMSOd6): δ 7.22 (s, 1H), 7.20 (s, 1H), 6.91 (bd s, 1H), 6.68 (bd s, 2H), 4.35 (m, 2H), 4.05 (dd, J=6.5, 11.5 Hz, 1H), 3.15 (m, 2H) Elemental Analysis: Elemental Analysis: Measured: C, 34.52; H, 3.22; N, 8.95; Cl, 22.64; S, 10.24 Calculated: C, 34.64; H, 2.68; N, 8.87; Cl, 22.94; S, 10.35.

EXAMPLE 11

(2S)-(−)-N-(7-Amino-2,3-dihydro-benzo[1,4]dioxin-2-ylmethyl)-sulfamide (Compound #36)

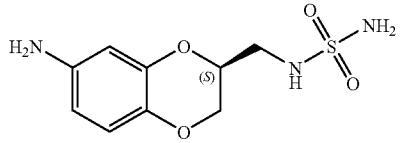

(2S)-(−)-N-(2,3-Dihydro-7-nitro-benzo[1,4]dioxin-2-yl-methyl)-sulfamide (1.2 g, 4.15 mmol), was prepared from 4-nitrocatechol according to the process outlined in Example 4. The (2S)-(−)-N-(2,3-Dihydro-7-nitro-benzo[1,4]dioxin-2-ylmethyl)-sulfamide, was then combined with 10% Pd/C in methanol (120 mL) and shaken under hydrogen atmosphere (39 psi) at room temperature for 3 h. The solids were filtered and washed with 10% M in DCM and the filtrate was evaporated in vacuo to yield crude product. The crude product was dissolved in 0.2 N HCl (25 mL), frozen and lyophilized to yield the title compound as a white flaky solid, as the corresponding hydrochloride salt.

MS (M+H)+ 260 ¹H NMR (DMSO d6): δ 10.2 (bd s, 3H), 6.86 (m, 1H), 6.85 (s, 1H), 6.74 (dd, J=2.5, 8.4 Hz, 1H), 4.22 (m, 2H), 3.88 (dd, J=6.7, 11.4 Hz, 1H), 3.04 (m, 2H)

EXAMPLE 12

(2S)-(−)-N-(7-Methyl-2,3-dihydro-benzo[1,4]dioxin-2-ylmethyl)-sulfamide (Compound #19)

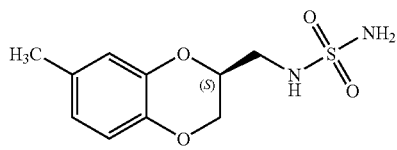

Title compound was prepared according to the procedure described in Example 4 above, starting with 4-methylcatechol, to yield a white solid, which was recrystallized from ethyl acetate/hexane to yield the title compound as a white solid.

MS [M−H]− 257 ¹H NMR (CDCl3): δ 6.76 (m, 1H), 6.66 (m, 2H), 4.80 (m, 1H), 4.57 (bd s, 1H), 4.40 (m, 1H), 4.28 (m, 1H), 4.03 (dd, J=6.9, 11.4 Hz, 1H), 3.45 (m, 2H), 2.25 (s, 3H). Elemental Analysis Calculated: C, 46.50; H, 5.46; N, 10.85; S, 12.41. Found: C, 46.65; H, 5.60; N, 10.84; S, 12.61.

EXAMPLE 13

Diabetic db/db Mouse In Vivo Assay

Db/db mice are known in the art to be susceptible to Type II diabetes (Sharma K, McCue P, Dunn S R. Am J Physiol Renal Physiol. 2003 June;284(6):F1138-44). The Db/db mice are also known in the art to be a useful model for dylipidemia.

Female db/db mice (C57BL/6J-Lep$^{db/db}$, Jackson Laboratories, Bar Harbor, Me., USA) were received at 8 weeks of age and single-housed and fed with regular chow diet. Blood was collected by tail puncture and glucose was monitored with a glucometer (OneTouch Basic, Lifescan, Newtown, Pa.).

Mice at 10 weeks of age were randomized into treatment groups based on glucose values (first criterion, average of 250 mg/dl) and body weight (second criterion, average of 37 gram). The mice were orally gavaged once daily (0.2 ml at 1500-1700 hour) with vehicle control (0.5% methylcellulose, pH7.4) and vehicle containing test compound (A300 mg/kg). On day 11, the mice were fasted for 4 hr during light cycle (food was removed 0600-1000 hour) and blood glucose levels were measured through tail puncture with a glucometer at 1000 hour. The mice were then anaesthetized with sodium pentobarbital (1 ml/kg, i.p, Sleepaway, Fort Dodge, Iowa) and blood was drawn via cardiac puncture and collected into heparinized tubes.

White adipose tissue (WAT) (retroperitoneal fat) and skeletal muscle (gastrocnemius and soleus muscle) were dissected and weighed. Plasma samples were obtained by centrifuge at 2,000 g for 15 minutes at 4° C. and subjected to measurement of insulin, HDL cholesterol and triglyceride.

Data shown below are expressed as the mean and standard error calculated using 9-10 mice per treatment group. The 2 tailed Student's t-Tests were used for statistic analysis. All animal studies complied with the guideline of the Institutional Animal Care and Use Committee.

Compound #8 was evaluated according to the procedure described above. The blood glucose levels of female db/db mice were 255±15 mg/dl at 5 days before the experiments. At the end of the experiment, the blood glucose levels of vehicle control mice were elevated 166% (420±22 mg/dl). The blood glucose levels in db/db mice were significantly lower with Compound #8 treatments compared to vehicle treated mice. Insulin levels in Compound #8 treated animals versus vehicle treated animals were not statistically different.

Mice treated with Compound #8 exhibited greater skeletal muscle mass versus vehicle treated animals. Additionally, there was no significant reduction of fat mass for Compound #8 treated animals. Compound #8 mice also showed significant decrease in the fat to lean mass ratio (vehicle: 27.9±1.4 vs. Compound #8: 23.4±0.9, p<0.01).

Additionally, the plasma HDL cholesterol levels in db/db mice treated with Compound #8 were higher, as compared to vehicle treated mice, whereas the blood triglyceride levels in db/db mice treated with Compound #8 were lower, as compared to vehicle treated mice.

A summary of the data for vehicle and Compound #8 treated mice measuring blood glucose levels, retroperitoneal fat, skeletal muscle mass, triglycerides and HDL cholesterol are as shown in Table 4, below.

TABLE 4

| Diabetic db/db Mice In Vivo Results | | | |
|---|---|---|---|
| | Blood Glucose (mg/dl) | Retroperitoneal Fat Weight (g) | Skeletal Muscle Weight (g) |
| Vehicle | 420 ± 21.9 | 1.47 ± 0.05 | 0.136 ± 0.01 |
| Compound #8 | 210 ± 27 | 1.31 ± 0.07 | 0.154 ± 0.00 |
| | p < 0.001 | | p < 0.05 |
| | Triglycerides (mg/dl) | HDL Cholesterol (mg/dl) | |
| Vehicle | 161 ± 57 | 45.5 ± 4.1 | |
| Compound #8 | 98 ± 41 | 55.9 ± 3.7 | |
| | p < 0.01 | p < 0.001 | |

Thus, the data show that Compound #8 was effective at (a) lowering blood glucose levels, (b) lowering triglycerides and (c) elevating HDL cholesterol levels. Additionally animals treated with Compound #8 had more muscle mass then those treated with vehicle, which suggests that Compound #8 may preserve muscle mass i.e. prevent diabetic cachexia.

EXAMPLE 14

Female db/db Mouse Assay

Compound #8 was suspended in 0.5% Methocel using a hand held homogenizer to reduce the particle size and a magnetic stir bar and stir plate to keep the particles homogeneously suspended throughout the dosing period. 0.5% Hydroxypropyl Methylcellulose (Methocel) used as vehicle/control. Compound #8 was tested in both diabetic models of mouse and rat.

Female diabetic db/db mice with hyperglycemia (blood glucose concentrations averaged 250 mg/dL) were used for glucose lowering effect studies. The average body weights of db/db mice were 37 grams. Db/db mice are susceptible to Type 2 diabetes. Female db/db mice (C57BL/6J-Lep$^{db/db}$, Jackson Laboratories, Bar Harbor, Me., USA) at 8 weeks of age were group housed, two per cage, and fed with regular chow diet (Laboratory rodent diet 5001). All of the mice were quarantined for a period of one week before transfer to the animal procedure room. A drop of blood (about 2 microliters) was collected by tail puncture and glucose concentration was detected with a glucometer (OneTouch UltraSmart, Lifescan, Milpitas, Calif.). Mice at 10 weeks of age were randomized into three treatment groups based on glucose values (first criterion, average of 250 mg/dL) and body weight (second criterion, average of 37 g). Animals were separated and single housed at least three days prior to the drug treatments to allow acclimation to the new surroundings.

The mice assay comprised two parts: In the first single dose part of Study A, 10 mice used as a negative control were given vehicle (0.5% Methocel); 10 mice were treated with 300 mg/kg Compound #8 JNJ-26489112 in vehicle; and mice used as positive control were treated with 20 mg/kg rosiglitazone (an insulin sensitizer that lowers glucose) in vehicle. In the second, dose response part of Study A, 48 mice were allocated into 4 treatment groups of 12 mice each. The four groups were then treated with 0.5% Methocel (vehicle), 10 mg/kg Compound #8, 30 mg/kg Compound #8, and 100 mg/kg Compound #8 in vehicle, respectively.

The mice were orally gavaged once daily (at 1500-1700 hour) with vehicle control (0.5% methocel, pH7.4) or vehicle containing Compound #8 for 10 days. The dosing volume was 5 mL/kg body weight (0.2 mL for 40 gram mice). The mice were fed ad lib throughout the study. A necropsy was completed 18 hours after last dosing.

Blood glucose levels were measured from blood collected through tail puncture using a glucometer at 1000 hour. The mice were anaesthetized with sodium pentobarbital (1 ml/kg, intraperitoneal [i.p.] injection, SleepAway, Fort Dodge, Iowa) and blood was drawn via cardiac puncture using 1 mL syringe and collected into heparinized tubes. White adipose tissues (WAT) (retroperitoneal and inguinal fat pads), brown adipose tissue (BAT) and skeletal muscles (gastrocnemius and soleus muscle) and stomach contents were dissected and weighed. Plasma samples were obtained by centrifuging whole blood at 2000~3000 g for 10~20 minutes at 4° C. and stored at −20° C. for further measurement of insulin, HDL, LDL, total cholesterol and triglyceride.

Plasma insulin concentrations were measured by in both studies using the appropriate rat/mouse insulin enzyme-linked immunosorbent assay (ELISA) kit (EZRMI-13K, LINCO Research, St. Charles, Mo.). Blood samples were diluted 1:4 in charcoal stripped mouse serum that was included in the ELISA kit. The rest of the procedure followed the manufacturers instruction. The total fluorescence was detected using an Orion 1 Microplate Luminometer (Berthold Detection Systems, Pforzheim, Germany).

Plasma total cholesterol, high density lipoprotein (HDL), low density lipoprotein (LDL) and triglyceride concentrations were measured by using a Bayer ADVIA 1650 blood chemistry analyzer (Bayer HealthCare LLC, Diagnostic Division, Tarrytown, N.Y.). According to manufacturers protocol, cholesterol measurement was an enzymatic method utilizing cholesterol esterase and cholesterol oxidase conversion followed by a Trinder endpoint; Elimination/catalase method was used for HDL measurement; an enzymatic method with a Trinder endpoint was used for triglyceride measurement.

Data from both parts of the Study (single dose and dose response) was analyzed using the standard two-tailed Student's t-test and are expressed below as means and standard errors.

In the single dose part of Study A, the average blood glucose levels of db/db mice were 255±15 mg/dL before dosing. As shown in Table 5 below, at the end of the experiment, the glucose levels of vehicle treated mice were elevated 166% (420±22 mg/dL). Glucose levels were reduced 50% in mice treated with Compound #8 at 300 mg/kg, compared to vehicle treated mice. This effect was similar to that observed with rosiglitazone treatment. There were no changes of insulin concentrations observed among drug treated mice and vehicle treated mice.

TABLE 5

| Treatment | Glucose (mg/dL) | Insulin (ng/ml) |
| --- | --- | --- |
| Vehicle | 420 ± 22 | 11.9 ± 2.2 |
| Rosiglitazone | 170 ± 23*** | 11.2 ± 2.3 |
| Compound #8 @ 300 mg/kg | 210 ± 27*** | 16.0 ± 2.5 |

***p < 0.001 versus vehicle value.

In the dose response part of Study A, as shown in Table 6 below, blood glucose was not affected by treatment with Compound #8 at 10, 30 or 100 mg/kg. In contrast, hyperinsulinemia in the mice treated with 100 mg/kg of Compound #8 was decreased by 63.5%, compared to vehicle treated mice.

TABLE 6

| Treatment | Glucose (mg/dL) | Insulin (ng/ml) |
| --- | --- | --- |
| Vehicle | 400 ± 29 | 10.7 ± 2.0 |
| Compound #8 @ 10 mg/kg | 420 ± 10 | 11.9 ± 2.5 |
| Compound #8 @ 30 mg/kg | 439 ± 13 | 10.8 ± 2.9 |
| Compound #8 @ 100 mg/kg | 394 ± 17 | 3.9 ± 1.4** |

**p < 0.01 versus vehicle value

In the single dose part of Study A, the vehicle control db/db mice showed dyslipidemia with high circulating triglyceride concentrations and low HDL, which resulted in a high ratio of triglyceride to HDL. As shown in Table 7 below, Compound #8, dosed at 300 mg/kg decreased plasma triglyceride by 39.4% and elevated HDL by 22.8% compared to the vehicle treated mice. Therefore the ratio of triglyceride to HDL was reduced by 50.2%, which reflects an improved lipid profile. This result was similar to the effect observed with rosiglitazone treatment. No changes in LDL levels were observed for the db/db mice treated with Compound #8, with mice treated with rosiglitazone or with vehicle.

TABLE 7

| Treatment | Triglyceride (mg/dL) | Cholesterol (mg/dL) | HDL (mg/dL) | LDL (mg/dL) | Ratio (Triglyceride to HDL) |
|---|---|---|---|---|---|
| Vehicle | 161 ± 18 | 91 ± 3 | 45.5 ± 1.3 | 3.1 ± 0.4 | 3.5 ± 0.3 |
| Rosiglitazone | 105 ± 23 | 123 ± 8** | 62.5 ± 3.2*** | 3.3 ± 0.3 | 1.6 ± 0.3*** |
| Compound #8 @ 300 mg/kg | 98 ± 13** | 108 ± 3 | 55.9 ± 1.2*** | 3.4 ± 0.2 | 1.8 ± 0.3*** |

**$p < 0.01$,
***$p < 0.001$ versus vehicle control

In the dose response part of Study A, mice were treated with 10, 30, and 100 mg/kg of Compound #8. Mice treated with 100 mg/kg of Compound #8 showed significantly decreased ratio of triglyceride to HDL, as shown in Table 8 below. The total cholesterol concentrations were elevated in both mice treated with Compound #8 (by 18.7%) and those treated with rosiglitazone (by 35.1%) relative to vehicle treated mice, respectively.

TABLE 8

| Treatment | Triglyceride (mg/dL) | Cholesterol (mg/dL) | HDL (mg/dL) | LDL (mg/dL) | Ratio (Triglyceride to HDL) |
|---|---|---|---|---|---|
| Vehicle | 204 ± 19 | 92 ± 2 | 46.2 ± 1.5 | ND | 4.5 ± 0.4 |
| Compound #8 @ 10 mg/kg | 166 ± 13 | 92 ± 3 | 47.1 ± 1.5 | ND | 3.5 ± 0.3 |
| Compound #8 @ 30 mg/kg | 202 ± 18 | 95 ± 2 | 49.2 ± 1.7 | ND | 4.1 ± 0.3 |
| Compound #8 @ 100 mg/kg | 169 ± 10 | 102 ± 3* | 51.7 ± 1.7* | ND | 3.3 ± 0.3* |

*$p < 0.05$ versus vehicle control.
ND: not detected

In both parts of Study A, food intake was monitored every three days for a period of nine days. In the first study, as shown in Table 9, the mice dosed with 300 mg/kg of Compound #8 had significantly decreased food intake compared to vehicle treated mice, whereas rosiglitazone treatment increased food intake. Despite the reduction of food intake, the body weights of mice treated with 300 mg/kg Compound #8 were not affected. The rosiglitazone treated mice had increased body weight (weight gain 3.1±0.4 g, $p<0.05$) compared to vehicle treated mice (weight gain: 0.3±0.2 g). At the end of the experiment, stomach content weights were two times greater in mice treated with 300 mg/kg of Compound #8 than in mice treated with vehicle.

TABLE 9

| | Total chow consumption (g) | | | Final weight (g) | |
|---|---|---|---|---|---|
| Treatment | Day 1-3 | Day 4-6 | Day 7-9 | Body weight | Stomach contents |
| Vehicle | 18 ± 1.2 | 22 ± 2.2 | 17 ± 0.6 | 40 ± 0.5 | 0.25 ± 0.04 |
| Rosiglitazone | 21 ± 0.8*** | 22 ± 0.9 | 19 ± 0.7 | 43 ± 1.0* | 0.32 ± 0.04 |
| Compound #8 @ 300 mg/kg | 14 ± 0.9** | 14.9 ± 1.1** | 16 ± 0.6* | 39 ± 0.9 | 0.52 ± 0.07** |

*$p < 0.05$,
***$p < 0.01$ versus vehicle control, respectively.

Skeletal muscle mass and brown adipose tissue weights in the db/db mice treated with Compound #8 at 300 mg/kg were greater than vehicle treated mice, as shown in Table 10 below. Additionally, the ratio of white adipose tissue to muscle was significantly reduced in Compound #8 treated mice, although no differences were found in inguinal fat and retroperitoneal fat pad weights between those groups.

TABLE 10

| Treatment | Inguinal fat (g) | Retro-peritoneal fat (g) | Muscle (g) | Brown Adipose Tissue (g) | Ratio[&] (fat/muscle) |
|---|---|---|---|---|---|
| Vehicle | 2.28 ± 0.17 | 1.47 ± 0.05 | 0.136 ± 0.01 | 0.17 ± 0.02 | 27.9 ± 1.4 |
| Rosiglitazone | 2.44 ± 0.11 | 1.45 ± 0.10 | 0.154 ± 0.00* | 0.32 ± 0.02*** | 25.4 ± 1.6 |
| Compound #8 @ 300 mg/kg | 2.28 ± 0.11 | 1.31 ± 0.07 | 0.154 ± 0.00* | 0.25 ± 0.01*** | 23.4 ± 0.9** |

[&]Fat/muscle ratio is calculated as: total weights of inguinal fat and retroperitoneal fat/muscle weight.
**p < 0.01,
***p < 0.001 versus vehicle control, respectively.

In the dose response part of Study A, as shown in Table 11 below, Compound #8 treatment at 10 mg/kg, 30 mg/kg, and 100 mg/kg, increased brown adipose tissue weights compared with vehicle treated mice. Increased stomach content was observed in mice given a 100 mg/kg dose of Compound #8 (drug treatment: 0.51±0.04 g vs control: 0.35±0.03 g, p<0.05), but not at lower doses. There were no differences observed for food intake and body weight in any of the groups. In Table 11 below, Fat/muscle ratio is calculated as total weights of inguinal fat and retroperitoneal fat/muscle weight.

TABLE 11

| Treatment | Inguinal fat (g) | Retro-peritoneal fat (g) | Muscle (g) | Brown Adipose Tissue (g) | Ratio (fat/muscle) |
|---|---|---|---|---|---|
| Vehicle | 2.08 ± 0.06 | 1.46 ± 0.09 | 0.132 ± 0.004 | 0.18 ± 0.01 | 27.0 ± 0.9 |
| Compound #8 @ 10 mg/kg | 2.15 ± 0.11 | 1.47 ± 0.04 | 0.140 ± 0.004 | 0.23 ± 0.01** | 25.9 ± 0.8 |
| Compound #8 @ 30 mg/kg | 1.97 ± 0.07 | 1.49 ± 0.07 | 0.141 ± 0.003 | 0.22 ± 0.01** | 24.5 ± 0.5* |
| Compound #8 @ 100 mg/kg | 2.05 ± 0.09 | 1.55 ± 0.11 | 0.140 ± 0.007 | 0.24 ± 0.00*** | 26.3 ± 1.0 |

*p < 0.05,
**p < 0.01,
***p < 0.001 versus vehicle control, respectively.

EXAMPLE 15

Zucker Diabetic Fatty Rats Assay

Compound #8 was suspended in 0.5% Methocel using a hand held homogenizer to reduce the particle size and a magnetic stir bar and stir plate to keep the particles homogeneously suspended throughout the dosing period. 0.5% Hydroxypropyl Methylcellulose (Methocel) used as vehicle/control. Compound #8 was tested in both diabetic models of mouse and rat.

In this study, female Zucker diabetic fatty (ZDF Gmi-fa/fa) rats were selected for glucose lowering effect and oral glucose tolerance test (OGTT) studies. ZDF rats from (Charles River Laboratories, Wilmington, Mass.) at 7 weeks of age were individually housed and fed with C13004 diet (obtained from Research Diets, New Brunswick, N.J.). All of the rats were quarantined for a period of one week before transfer to the animal procedure room. A drop of blood (about 2 microliters) was collected by tail puncture and glucose concentration was detected with a glucometer (OneTouch UltraSmart, Lifescan, Milpitas, Calif.).

ZDF rats at 8 weeks of age were randomized into four treatment groups based on glucose values (first criterion, average of 150 mg/dL) and body weight (second criterion, average of 240 g). 32 rats were allocated into 4 treatment groups of 8 rats each. The four groups were then treated with 0.5% Methocel (vehicle), 10 mg/kg Compound #8, 30 mg/kg Compound #8, and 100 mg/kg Compound #8 in vehicle, respectively.

The rats were orally gavaged once daily (at 1500-1700 hour) with vehicle control (0.5% Methocel, pH7.4) or vehicle containing Compound #8 for 7 days. The dosing volume was 5 mL/kg body weight (1.2 mL for 250 gram rat). The rats were fed ad lib throughout the study.

Basal glucose levels after treatments were measured on Day 4 and Day 6 in 2 hour fasted rats with a glucometer (OneTouch UltraSmart, Lifescan, Milpitas, Calif.) after collecting two microliters of blood through tail puncture. Oral Glucose Tolerance Test (OGTT) was performed on Day 7 in 4 hour-fasted rats. Two hours after being dosed with Compound #8 or vehicle, the rats were gavaged with a 2g/kg of 50% glucose solution right after basal glucose levels measurement (0 minute). Blood glucose levels were then measured at 30, 60, 90 and 120 minutes through tail puncture.

On Day 8, rats were anaesthetized with sodium pentobarbital (1 ml/kg, intraperitoneal [i.p.] injection, SleepAway, Fort Dodge, Iowa) and blood was drawn via cardiac puncture using 3 mL syringe and collected into heparinized tubes. Plasma samples were obtained by centrifuging whole blood at 2000~3000 g for 10~20 minutes at 4° C. and stored at −20° C. for further measurement of insulin, HDL, total cholesterol and triglyceride.

Plasma insulin concentrations were measured by in both studies using the appropriate rat/mouse insulin enzyme-linked immunosorbent assay (ELISA) kit (EZRMI-13K, LINCO Research, St. Charles, Mo.). Blood samples were diluted 1:4 in charcoal stripped mouse serum that was included in the ELISA kit. The rest of the procedure followed the manufacturers instruction. The total fluorescence was detected using an Orion 1 Microplate Luminometer (Berthold Detection Systems, Pforzheim, Germany).

Plasma total cholesterol, high density lipoprotein (HDL), low density lipoprotein (LDL) and triglyceride concentrations were measured by using a Bayer ADVIA 1650 blood chemistry analyzer (Bayer HealthCare LLC, Diagnostic Division, Tarrytown, N.Y.). According to manufacturers protocol, cholesterol measurement was an enzymatic method utilizing cholesterol esterase and cholesterol oxidase conversion followed by a Trinder endpoint; Elimination/catalase method was used for HDL measurement; an enzymatic method with a Trinder endpoint was used for triglyceride measurement.

Data from this study was analyzed using the standard two-tailed Student's t-test and are expressed below as means and standard errors.

In Study B with the Zucker diabetic rats, as shown in Table 12, treatment with 30 mg/day or 100 mg/kg per day of Compound #8 resulted in dose and time dependent glucose lowering effects on Day 4 and Day 6.

TABLE 12-continued

| Treatment | Day 0 | Day 4 | Day 6 |
|---|---|---|---|
| Compound #8 @ 100 mg/kg | 147 ± 7 | 125 ± 4** | 134 ± 5** |

*p < 0.05,
**p < 0.01 versus vehicle control, respectively.

As shown in Table 13, OGTT performed on Day 7 showed improved glucose and insulin profile for rats treated with Compound #8 in a dose-dependent manner. After glucose challenge, there were sustained high glucose levels that lasted to 60 minutes in vehicle control rats, whereas rats treated with 100 mg/kg of Compound #8 had lower glucose levels that peaked at 30 minutes. Analysis of the area under the curve (AUC) for blood glucose were also significantly decreased in the ZDF rats treated with Compound #8 at 30 mg/kg and 100 mg/kg dose levels as compared to the vehicle-treated group.

TABLE 13

| Treatment | 0 min | 30 min | 60 min | 90 min | 120 min | AUC (min × mg/dL) |
|---|---|---|---|---|---|---|
| Vehicle | 213 ± 37 | 314 ± 40 | 343 ± 38 | 314 ± 35 | 278 ± 33 | 38651 ± 4276 |
| Compound #8 @ 10 mg/kg | 186 ± 30 | 281 ± 30 | 316 ± 33 | 293 ± 24 | 252 ± 30 | 33279 ± 3607 |
| Compound #8 @ 30 mg/kg | 163 ± 18 | 244 ± 24 | 263 ± 18 | 253 ± 23* | 221 ± 18** | 28556 ± 2477* |
| Compound #8 @ 100 mg/kg | 123 ± 5* | 209 ± 14** | 200 ± 10** | 175 ± 8*** | 145 ± 7*** | 21529 ± 984*** |

*p < 0.05,
**p < 0.01,
***p < 0.001 versus vehicle control, respectively.

TABLE 12

| Treatment | Day 0 | Day 4 | Day 6 |
|---|---|---|---|
| Vehicle | 149 ± 9 | 182 ± 16 | 216 ± 26 |
| Compound #8 @ 10 mg/kg | 153 ± 13 | 148 ± 15 | 190 ± 28 |
| Compound #8 @ 30 mg/kg | 152 ± 11 | 146 ± 9 | 151 ± 11* |

As shown in Table 14, treatment with 100 mg/kg of Compound #8 significantly decreased plasma insulin by 32% and triglyceride levels on Day 8. The ratio of triglyceride to HDL was reduced by 59%. This result was consistent with the effect observed in db/db mice with Compound #8 treatment, except that the effective dose in ZDF rats was lower by two third of the dose in db/db mice. No reduction in food intake reduction or weight loss was observed in any of the groups in the Zucker rat study.

TABLE 14

| Treatment | Insulin (ng/mL) | Triglyceride (mg/dL) | Cholesterol (mg/dL) | HDL (mg/dL) | Ratio (Triglyceride to HDL) |
|---|---|---|---|---|---|
| Vehicle | 13 ± 1.3 | 1692 ± 224 | 159 ± 10 | 37 ± 1.2 | 46 ± 6 |
| Compound #8 @ 10 mg/kg | 16 ± 1.0 | 1323 ± 124 | 142 ± 6 | 36 ± 1.0 | 37 ± 3 |

TABLE 14-continued

| Treatment | Insulin (ng/mL) | Triglyceride (mg/dL) | Cholesterol (mg/dL) | HDL (mg/dL) | Ratio (Triglyceride to HDL) |
|---|---|---|---|---|---|
| Compound #8 @ 30 mg/kg | 14 ± 1.1 | 1383 ± 254 | 144 ± 11 | 36 ± 1.1 | 39 ± 7 |
| Compound #8 @ 100 mg/kg | 8.8 ± 1.2* | 776 ± 119** | 134 ± 7 | 41 ± 2.2 | 19 ± 3*** |

*p < 0.05,
**p < 0.01,
***p < 0.001 versus vehicle control.

EXAMPLE 16

Zucker Diabetic Fatty Rats Assay

Compound #8 was suspended in 0.5% Methocel using a hand held homogenizer to reduce the particle size and a magnetic stir bar and stir plate to keep the particles homogeneously suspended throughout the dosing period. 0.5% Hydroxypropyl Methylcellulose (Methocel) used as vehicle/control. Compound #8 was tested in both diabetic models of mouse and rat.

In this study, female Zucker diabetic fatty (ZDF Gmi-fa/fa) rats were selected for glucose lowering effect. ZDF rats from (Charles River Laboratories, Wilmington, Mass.) at 7 weeks of age were individually housed and fed with C13004 diet (obtained from Research Diets, New Brunswick, N.J.). All of the rats were quarantined for a period of one week before transfer to the animal procedure room. A drop of blood (about 2 microliters) was collected by tail puncture and glucose concentration was detected with a glucometer (OneTouch UltraSmart, Lifescan, Milpitas, Calif.).

ZDF rats at 8 weeks of age were randomized into four treatment groups based on glucose values (first criterion, average of 150 mg/dL) and body weight (second criterion, average of 240 g). 13 rats were allocated into 4 treatment groups of 3 rats each for Compound #8 treated groups and 4 rats for the non-treated group. The three groups were then treated with 10 mg/kg Compound #8, 30 mg/kg Compound #8, and 100 mg/kg Compound #8 in 0.5 methylcellulose, respectively.

The rats were orally gavaged once daily (at 1500-1700 hour) with vehicle control (0.5% Methocel, pH7.4) or vehicle containing Compound #8 for 7 days. The dosing volume was 5 mL/kg body weight (1.2 mL for 250 gram rat). The rats were fed ad lib throughout the study. The rats were then allowed 29 days of wash-out period, where no dosing was administered.

Basal glucose levels after treatments were measured on Day 0 (baseline) and Day 36 (after 7 days dosing and 29 days wash-out) in ad lib fed rats with a glucometer (OneTouch UltraSmart, Lifescan, Milpitas, Calif.) after collecting two microliters of blood through tail puncture.

Data from this study was analyzed using the standard two-tailed Student's t-test and are expressed below as means and standard errors, with results as listed in Table 15 below. Treatment with Compound #8 at 30 and 100 mg/kg showed a statistically significant (p<0.01) decreased blood glucose levels even after the 29 day washout period.

TABLE 15

| Treatment | Blood Glucose Level (mg/dL) | |
|---|---|---|
| | Day 0 | Day 36 |
| No treatment (n = 4) | 230 ± 63 | 379 ± 20 |
| Compound #8 @ 10 mg/kg (n = 3) | 222 ± 20 | 295 ± 81 |
| Compound #8 @ 30 mg/kg (n = 3) | 229 ± 23 | 247 ± 86** |
| Compound #8 @ 100 mg/kg (n = 3) | 228 ± 18 | 219 ± 39** |

**p < 0.01 versus vehicle control

EXAMPLE 17

As a specific embodiment of an oral composition, 100 mg of the Compound #8 prepared as in Example 7 is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A method for a glucose related disorder selected from the from the group consisting of elevated glucose level, pre-diabetes, impaired oral glucose tolerance, poor glycemic control, Type II Diabetes Mellitus, Syndrome X (also known as metabolic syndrome), gestational diabetes, insulin resistance, hyperglycemia and loss of muscle mass as a results of hyperglycemia comprising administering to a subject in need thereof, a therapeutically effective amount of a compound of formula (I)

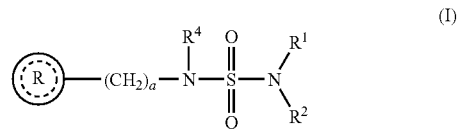

wherein
$R^1$ and $R^2$ are each independently selected from the group consisting of hydrogen and lower alkyl;
$R^4$ is selected from the group consisting of hydrogen and lower alkyl;
a is an integer from 1 to 2;

is selected from the group consisting of

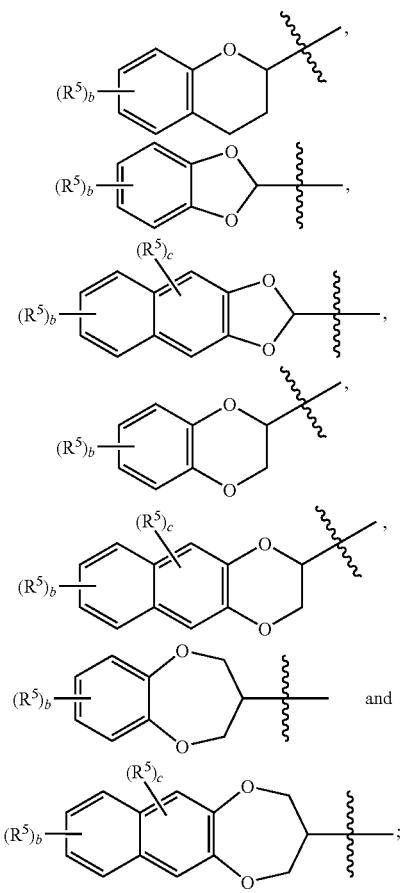

and

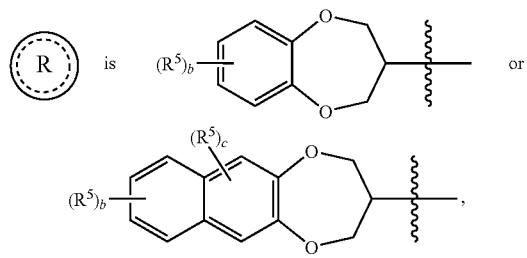

wherein b is an integer from 0 to 4; and wherein c is an integer from 0 to 2;

each $R^5$ is independently selected from the group consisting of halogen, lower alkyl and nitro;

provided that when then a is 1;

or a pharmaceutically acceptable salt thereof.

2. The method as in claim 1, wherein $R^1$ and $R^2$ are each independently selected from the group consisting of hydrogen and lower alkyl;

$R^4$ is selected from the group consisting of hydrogen and lower alkyl;

a is an integer from 1 to 2;

is selected from the group consisting of

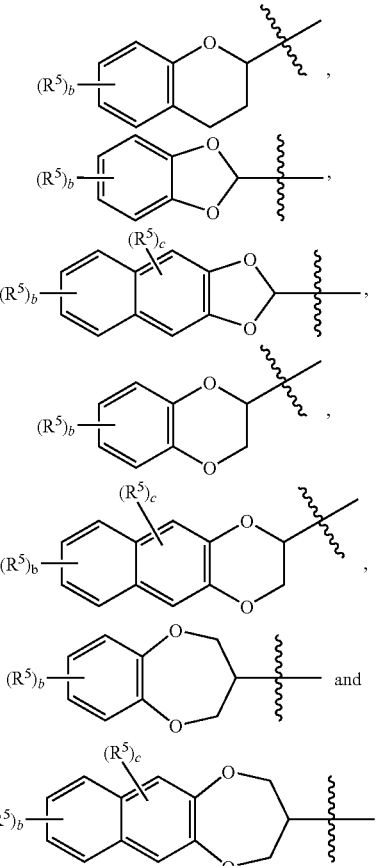

and

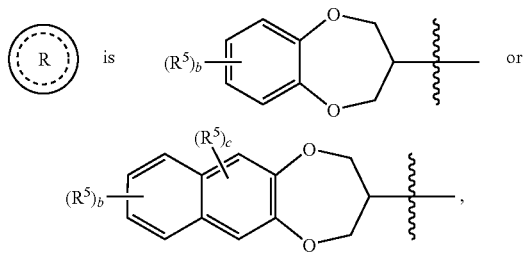

wherein b is an integer from 0 to 2; and wherein c is an integer from 0 to 1;

each $R^5$ is independently selected from the group consisting of halogen, lower alkyl and nitro;

provided that when then a is 1;

or a pharmaceutically acceptable salt thereof.

3. The method as in claim 2, wherein $R^1$ and $R^2$ are each independently selected from the group consisting of hydrogen and lower alkyl;

R⁴ is selected from the group consisting of hydrogen and lower alkyl;

a is an integer from 1 to 2;

is selected from the group consisting of

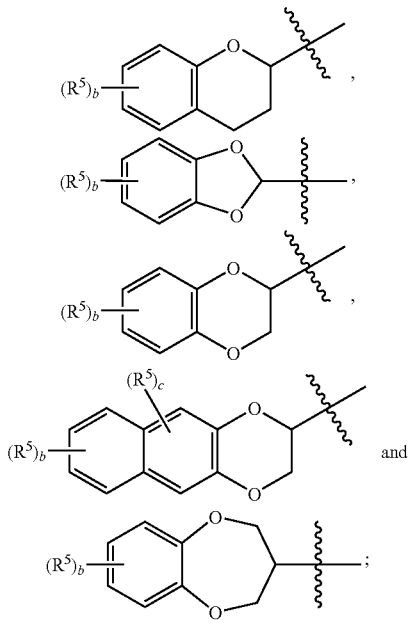

wherein b is an integer from 0 to 2; and wherein c is 0;
each R⁵ is independently selected from the group consisting of halogen, lower alkyl and nitro;
provided that when

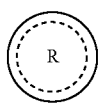

then a is 1;
or a pharmaceutically acceptable salt thereof.

4. The method as in claim 3, wherein
R¹ and R² are each independently selected from the group consisting of hydrogen and lower alkyl;
R⁴ is selected from the group consisting of hydrogen and methyl;
a is an integer from 1 to 2;

is selected from the group consisting of 2-(2,3-dihydro-benzo[1,4]dioxinyl), 2-(benzo[1,3]dioxolyl), 2-(3,4-dihydro-2H-benzo[1,4]dioxepinyl), 2-(6-chloro-2,3-dihydro-benzo[1,4]dioxinyl), 2-(6-fluoro-2,3-dihydro-benzo[1,4]dioxinyl), 2-(chromanyl), 2-(5-fluoro-2,3-dihydro-benzo[1,4]dioxinyl), 2-(7-chloro-2,3-dihydro-benzo[1,4]dioxinyl), 2-(6-chloro-benzo[1,3]dioxolyl), 2-(7-nitro-2,3-dihydro-benzo[1,4]dioxinyl), 2-(7-methyl-2,3-dihydro-benzo[1,4]dioxinyl), 2-(5-chloro-2,3-dihydro-benzo[1,4]dioxinyl), 2-(6-bromo-2,3-dihydro-benzo[1,4]dioxinyl), 2-(6,7-dichloro-2,3-dihydro-benzo[1,4]dioxinyl), 2-(8-chloro-2,3-dihydro-benzo[1,4]dioxinyl), 2-(2,3-dihydro-naphtho[2,3-b][1,4]dioxinyl) and 2-(4-methyl-benzo[1,3]dioxolyl);
provided that when

is 2-(3,4-dihydro-2H-benzo[1,4]dioxepinyl), then a is 1;
or a pharmaceutically acceptable salt thereof.

5. The method as in claim 4, wherein
R¹ and R² are each independently selected from the group consisting of hydrogen and methyl;
R⁴ is selected from the group consisting of hydrogen and methyl;
a is an integer from 1 to 2;

is selected from the group consisting of 2-(benzo[1,3]dioxolyl), 2-(2,3-dihydro-benzo[1,4]dioxinyl), 2-(6-chloro-2,3-dihydro-benzo[1,4]dioxinyl), 2-(7-chloro-2,3-dihydro-benzo[1,4]dioxinyl), 2-(7-methyl-2,3-dihydro-benzo[1,4]dioxinyl), 2-(6-bromo-2,3-dihydro-benzo[1,4]dioxinyl) and 2-(6,7-dichloro-2,3-dihydro-benzo[1,4]dioxinyl);
or a pharmaceutically acceptable salt thereof.

6. The method of claim 1, wherein the compound of formula (I) is selected from the group consisting of (2S)-(−)-N-(6-chloro-2,3-dihydro-benzo[1,4]dioxin-2-ylmethyl)-sulfamide; and pharmaceutically acceptable salts thereof.

7. A method of treating a glucose related disorder selected from the from the group consisting of elevated glucose level, pre-diabetes, impaired oral glucose tolerance, Type II Diabetes Mellitus, Syndrome X (also known as metabolic syndrome), gestational diabetes, insulin resistance, and hyperglycemia comprising administering to a subject in need thereof a therapeutically effective amount of a compound selected from the group consisting (2S)-(−)-N-(6-chloro-2,3-dihydro-benzo[1,4]dioxin-2-ylmethyl)-sulfamide; and pharmaceutically acceptable salts thereof.

8. The method of claim 1, wherein the glucose related disorder is selected from the group consisting of elevated glucose levels and Type II diabetes mellitus.

9. The method of claim 7, wherein the glucose related disorder is selected from the group consisting of elevated glucose levels and Type II diabetes mellitus.

10. A method for treating Type II Diabetes Mellitus comprising administering to a subject in need thereof a therapeutically effective amount of a compound of formula (II)
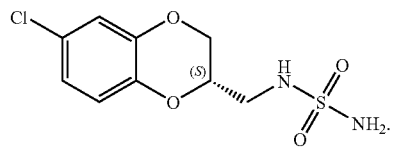
* * * * *